United States Patent
Moore et al.

(10) Patent No.: US 9,898,039 B2
(45) Date of Patent: Feb. 20, 2018

(54) MODULAR SMART NECKLACE

(71) Applicant: Toyota Motor Engineering & Manufacturing North America, Inc., Erlanger, KY (US)

(72) Inventors: Douglas A. Moore, Livermore, CA (US); Tiffany L. Chen, San Jose, CA (US); Rajiv Dayal, Santa Clara, CA (US)

(73) Assignee: TOYOTA MOTOR ENGINEERING & MANUFACTURING NORTH AMERICA, INC., Erlanger, KS (US)

( * ) Notice: Subject to any disclaimer, the term of this patent is extended or adjusted under 35 U.S.C. 154(b) by 0 days.

(21) Appl. No.: 14/817,028

(22) Filed: Aug. 3, 2015

(65) Prior Publication Data
US 2017/0038792 A1   Feb. 9, 2017

(51) Int. Cl.
*G06F 1/16* (2006.01)
*G01C 21/36* (2006.01)
(Continued)

(52) U.S. Cl.
CPC .......... *G06F 1/163* (2013.01); *A61B 5/02438* (2013.01); *G01C 21/36* (2013.01);
(Continued)

(58) Field of Classification Search
CPC ...... G06F 1/163; G06F 1/1615; G06F 1/1635; G06F 1/1683; G06F 1/1681; A61B 5/02438
(Continued)

(56) References Cited

U.S. PATENT DOCUMENTS 4,520,501 A   5/1985   DuBrucq
4,586,827 A   5/1986   Hirsch et al.
(Continued)

FOREIGN PATENT DOCUMENTS

CN   201260746   6/2009
CN   101527093   9/2009
(Continued)

OTHER PUBLICATIONS http://www.mightycast.com/#faq; 4 pages; May 19, 2015.
(Continued)

*Primary Examiner* — Nidhi Thaker
(74) *Attorney, Agent, or Firm* — Snell & Wilmer L.L.P.

(57) ABSTRACT

A smart necklace includes a first pod having a proximate connector and a component electrically coupled to the proximate connector that can receive input data or output data. The necklace also includes a second pod having a proximate connector and a component electrically coupled to the proximate connector that can receive input data or output data. The necklace also includes a curved main unit having a first connector removably, pivotably and electrically coupled to the proximate connector of the first pod and a second connector configured to be removably, pivotably and electrically coupled to the proximate connector of the second pod. The main unit also includes a mobile processor for receiving the input data from at least one of the first pod or the second pod, determining output data based on the input data, and outputting the output data via the first pod or the second pod.

17 Claims, 11 Drawing Sheets

(51) Int. Cl.
*H04M 1/05* (2006.01)
*A61B 5/024* (2006.01)
*H01R 24/60* (2011.01)
*H04N 5/225* (2006.01)
*H04M 1/02* (2006.01)

(52) U.S. Cl.
CPC ....... *G01C 21/3602* (2013.01); *G06F 1/1615* (2013.01); *G06F 1/1635* (2013.01); *G06F 1/1683* (2013.01); *H01R 24/60* (2013.01); *H04M 1/05* (2013.01); *H04N 5/225* (2013.01); *H04M 1/0254* (2013.01)

(58) Field of Classification Search
USPC .. 361/679.01–679.3, 679.55–679.59, 679.03
See application file for complete search history.

(56) References Cited

U.S. PATENT DOCUMENTS

| | | |
|---|---|---|
| 4,786,966 A | 11/1988 | Hanson |
| 5,047,952 A | 9/1991 | Kramer |
| 5,097,856 A | 3/1992 | Chi-Sheng |
| 5,129,716 A | 7/1992 | Holakovszky et al. |
| 5,265,272 A | 11/1993 | Kurcbart |
| 5,463,428 A | 10/1995 | Lipton et al. |
| 5,508,699 A | 4/1996 | Silverman |
| 5,539,665 A | 7/1996 | Lamming et al. |
| 5,543,802 A | 8/1996 | Villevieille |
| 5,544,050 A | 8/1996 | Abe |
| 5,568,127 A | 10/1996 | Bang |
| 5,636,038 A | 6/1997 | Lynt |
| 5,659,764 A | 8/1997 | Sakiyama |
| 5,701,356 A | 12/1997 | Stanford et al. |
| 5,733,127 A | 3/1998 | Mecum |
| 5,807,111 A | 9/1998 | Schrader |
| 5,872,744 A | 2/1999 | Taylor |
| 5,953,693 A | 9/1999 | Sakiyama |
| 5,956,630 A | 9/1999 | Mackey |
| 5,982,286 A | 11/1999 | Vanmoor |
| 6,009,577 A | 1/2000 | Day |
| 6,055,048 A | 4/2000 | Langevin et al. |
| 6,067,112 A | 5/2000 | Wellner et al. |
| 6,199,010 B1 | 3/2001 | Richton |
| 6,229,901 B1 | 5/2001 | Mickelson et al. |
| 6,230,135 B1 | 5/2001 | Ramsay |
| 6,230,349 B1 | 5/2001 | Silver et al. |
| 6,285,757 B1 | 9/2001 | Carroll et al. |
| 6,307,526 B1 | 10/2001 | Mann |
| 6,323,807 B1 | 11/2001 | Golding et al. |
| 6,349,001 B1 | 2/2002 | Spitzer |
| 6,466,232 B1 | 10/2002 | Newell |
| 6,477,239 B1 | 11/2002 | Ohki |
| 6,542,623 B1 | 4/2003 | Kahn |
| 6,580,999 B2 | 6/2003 | Maruyama et al. |
| 6,594,370 B1 | 7/2003 | Anderson |
| 6,603,863 B1 | 8/2003 | Nagayoshi |
| 6,619,836 B1 | 9/2003 | Silvant et al. |
| 6,701,296 B1 | 3/2004 | Kramer |
| 6,774,788 B1 | 8/2004 | Balfe |
| 6,825,875 B1 | 11/2004 | Strub et al. |
| 6,826,477 B2 | 11/2004 | Ladetto et al. |
| 6,834,373 B2 | 12/2004 | Dieberger |
| 6,839,667 B2 | 1/2005 | Reich |
| 6,857,775 B1 | 2/2005 | Wilson |
| 6,920,229 B2 | 7/2005 | Boesen |
| D513,997 S | 1/2006 | Wilson |
| 7,027,874 B1 | 4/2006 | Sawan et al. |
| D522,300 S | 6/2006 | Roberts |
| 7,069,215 B1 | 6/2006 | Bangalore |
| 7,106,220 B2 | 9/2006 | Gourgey et al. |
| 7,228,275 B1 | 6/2007 | Endo |
| 7,299,034 B2 | 11/2007 | Kates |
| 7,308,314 B2 | 12/2007 | Havey et al. |
| 7,336,226 B2 | 2/2008 | Jung et al. |
| 7,356,473 B2 | 4/2008 | Kates |
| 7,413,554 B2 | 8/2008 | Kobayashi et al. |
| 7,417,592 B1 | 8/2008 | Hsiao et al. |
| 7,428,429 B2 | 9/2008 | Gantz et al. |
| 7,463,188 B1 | 12/2008 | McBurney |
| 7,496,445 B2 | 2/2009 | Mohsini |
| 7,501,958 B2 | 3/2009 | Saltzstein et al. |
| 7,564,469 B2 | 7/2009 | Cohen |
| 7,565,295 B1 | 7/2009 | Hernandez-Rebollar |
| 7,598,976 B2 | 10/2009 | Sofer et al. |
| 7,618,260 B2 | 11/2009 | Daniel et al. |
| D609,818 S | 2/2010 | Tsang et al. |
| 7,656,290 B2 | 2/2010 | Fein et al. |
| 7,659,915 B2 | 2/2010 | Kurzweil et al. |
| 7,743,996 B2 | 6/2010 | Maciver |
| D625,427 S | 10/2010 | Lee |
| 7,843,488 B2 | 11/2010 | Stapleton |
| 7,848,512 B2 | 12/2010 | Eldracher |
| 7,864,991 B2 | 1/2011 | Espenlaub et al. |
| 7,938,756 B2 | 5/2011 | Rodetsky et al. |
| 7,991,576 B2 | 8/2011 | Roumeliotis |
| 8,005,263 B2 | 8/2011 | Fujimura |
| 8,035,519 B2 | 10/2011 | Davis |
| D649,655 S | 11/2011 | Petersen |
| 8,123,660 B2 | 2/2012 | Kruse et al. |
| D656,480 S | 3/2012 | McManigal et al. |
| 8,138,907 B2 | 3/2012 | Barbeau et al. |
| 8,150,107 B2 | 4/2012 | Kurzweil et al. |
| 8,177,705 B2 | 5/2012 | Abolfathi |
| 8,239,032 B2 | 8/2012 | Dewhurst |
| 8,253,760 B2 | 8/2012 | Sako et al. |
| 8,300,862 B2 | 10/2012 | Newton et al. |
| 8,306,673 B1 * | 11/2012 | Manning ............... A63C 17/12 280/87.041 |
| 8,325,263 B2 | 12/2012 | Kato et al. |
| D674,501 S | 1/2013 | Petersen |
| 8,359,122 B2 | 1/2013 | Koselka et al. |
| 8,395,968 B2 | 3/2013 | Vartanian et al. |
| 8,401,785 B2 | 3/2013 | Cho et al. |
| 8,414,246 B2 | 4/2013 | Tobey |
| 8,418,705 B2 | 4/2013 | Ota et al. |
| 8,428,643 B2 | 4/2013 | Lin |
| 8,483,956 B2 | 7/2013 | Zhang |
| 8,494,507 B1 | 7/2013 | Tedesco et al. |
| 8,494,859 B2 | 7/2013 | Said |
| 8,538,687 B2 | 9/2013 | Plocher et al. |
| 8,538,688 B2 | 9/2013 | Prehofer |
| 8,571,860 B2 | 10/2013 | Strope |
| 8,583,282 B2 | 11/2013 | Angle et al. |
| 8,588,464 B2 | 11/2013 | Albertson et al. |
| 8,588,972 B2 | 11/2013 | Fung |
| 8,594,935 B2 | 11/2013 | Cioffi et al. |
| 8,606,316 B2 | 12/2013 | Evanitsky |
| 8,610,879 B2 | 12/2013 | Ben-Moshe et al. |
| 8,630,633 B1 | 1/2014 | Tedesco et al. |
| 8,676,274 B2 | 3/2014 | Li |
| 8,676,623 B2 | 3/2014 | Gale et al. |
| 8,694,251 B2 | 4/2014 | Janardhanan et al. |
| 8,704,902 B2 | 4/2014 | Naick et al. |
| 8,743,145 B1 | 6/2014 | Price |
| 8,750,898 B2 | 6/2014 | Haney |
| 8,768,071 B2 | 7/2014 | Tsuchinaga et al. |
| 8,786,680 B2 | 7/2014 | Shiratori |
| 8,797,141 B2 | 8/2014 | Best et al. |
| 8,797,386 B2 | 8/2014 | Chou et al. |
| 8,803,699 B2 | 8/2014 | Foshee et al. |
| 8,814,019 B2 | 8/2014 | Dyster et al. |
| 8,825,398 B2 | 9/2014 | Alexandre |
| 8,836,532 B2 | 9/2014 | Fish, Jr. et al. |
| 8,836,580 B2 | 9/2014 | Mendelson |
| 8,836,910 B2 | 9/2014 | Cashin et al. |
| 8,902,303 B2 | 12/2014 | Na'Aman et al. |
| 8,909,534 B1 | 12/2014 | Heath |
| D721,673 S | 1/2015 | Park et al. |
| 8,926,330 B2 | 1/2015 | Taghavi |
| 8,930,458 B2 | 1/2015 | Lewis |
| 8,981,682 B2 | 3/2015 | Delson et al. |
| 8,994,498 B2 * | 3/2015 | Agrafioti ............... G06F 21/40 340/5.52 |

(56) References Cited

U.S. PATENT DOCUMENTS

| | | | |
|---|---|---|---|
| D727,194 S | 4/2015 | Wilson |
| 9,004,330 B2 | 4/2015 | White |
| 9,025,016 B2 | 5/2015 | Wexler et al. |
| 9,053,094 B2 | 6/2015 | Yassa |
| 9,076,450 B1 | 7/2015 | Sadek |
| 9,081,079 B2 | 7/2015 | Chao et al. |
| 9,081,385 B1 | 7/2015 | Ferguson |
| D736,741 S | 8/2015 | Katz |
| 9,111,545 B2 | 8/2015 | Jadhav et al. |
| D738,238 S | 9/2015 | Pede et al. |
| 9,137,484 B2 | 9/2015 | Difrancesco et al. |
| 9,137,639 B2 | 9/2015 | Garin et al. |
| 9,140,554 B2 | 9/2015 | Jerauld |
| 9,148,191 B2 | 9/2015 | Teng et al. |
| 9,158,378 B2 | 10/2015 | Hirukawa |
| D742,535 S | 11/2015 | Wu |
| D743,933 S | 11/2015 | Park et al. |
| 9,190,058 B2 | 11/2015 | Klein |
| 9,230,430 B2 | 1/2016 | Civelli et al. |
| 9,267,801 B2 | 2/2016 | Gupta et al. |
| 9,269,015 B2 | 2/2016 | Boncyk |
| 9,304,588 B2 | 4/2016 | Aldossary |
| D756,958 S | 5/2016 | Lee et al. |
| D756,959 S | 5/2016 | Lee et al. |
| 9,335,175 B2 | 5/2016 | Zhang et al. |
| 9,341,014 B2 | 5/2016 | Oshima et al. |
| 9,355,547 B2 | 5/2016 | Stevens et al. |
| 9,367,087 B1 * | 6/2016 | Townsend | G06F 1/163 |
| 2001/0023387 A1 | 9/2001 | Rollo |
| 2002/0067282 A1 | 6/2002 | Moskowitz et al. |
| 2002/0071277 A1 | 6/2002 | Starner et al. |
| 2002/0075323 A1 | 6/2002 | O'Dell |
| 2002/0173346 A1 | 11/2002 | Wang |
| 2002/0178344 A1 | 11/2002 | Bourguet |
| 2003/0026461 A1 | 2/2003 | Arthur Hunter |
| 2003/0133085 A1 | 7/2003 | Tretiakoff et al. |
| 2003/0179133 A1 | 9/2003 | Pepin et al. |
| 2004/0037051 A1 * | 2/2004 | Hagiwara | G06F 1/163 |
| | | | 361/749 |
| 2004/0056907 A1 | 3/2004 | Sharma |
| 2004/0232179 A1 | 11/2004 | Chauhan |
| 2004/0267442 A1 | 12/2004 | Fehr et al. |
| 2005/0052852 A1 * | 3/2005 | Ono | G06F 1/163 |
| | | | 361/749 |
| 2005/0020845 A1 | 9/2005 | Fink et al. |
| 2005/0221260 A1 | 10/2005 | Kikuchi |
| 2005/0283752 A1 | 12/2005 | Fruchter |
| 2006/0004512 A1 | 1/2006 | Herbst |
| 2006/0028550 A1 | 2/2006 | Palmer |
| 2006/0029256 A1 | 2/2006 | Miyoshi |
| 2006/0129308 A1 | 6/2006 | Kates |
| 2006/0171704 A1 | 8/2006 | Bingle et al. |
| 2006/0177086 A1 | 8/2006 | Rye et al. |
| 2006/0184318 A1 | 8/2006 | Yoshimine |
| 2006/0292533 A1 | 12/2006 | Selod |
| 2007/0001904 A1 | 1/2007 | Mendelson |
| 2007/0052672 A1 | 3/2007 | Ritter et al. |
| 2007/0173688 A1 | 7/2007 | Kim |
| 2007/0230786 A1 | 10/2007 | Foss |
| 2007/0296572 A1 | 12/2007 | Fein |
| 2008/0024594 A1 | 1/2008 | Ritchey |
| 2008/0068559 A1 | 3/2008 | Howell |
| 2008/0120029 A1 | 5/2008 | Zelek et al. |
| 2008/0145822 A1 | 6/2008 | Bucchieri |
| 2008/0174676 A1 | 7/2008 | Squilla et al. |
| 2008/0198222 A1 | 8/2008 | Gowda |
| 2008/0198324 A1 | 8/2008 | Fuziak |
| 2008/0208455 A1 | 8/2008 | Hartman |
| 2008/0251110 A1 | 10/2008 | Pede |
| 2008/0260210 A1 | 10/2008 | Kobeli |
| 2009/0012788 A1 | 1/2009 | Gilbert |
| 2009/0040215 A1 | 2/2009 | Afzulpurkar |
| 2009/0106016 A1 | 4/2009 | Athsani |
| 2009/0118652 A1 | 5/2009 | Carlucci |
| 2009/0122161 A1 | 5/2009 | Bolkhovitinov |
| 2009/0122648 A1 | 5/2009 | Mountain et al. |
| 2009/0157302 A1 | 6/2009 | Tashev et al. |
| 2009/0177437 A1 | 7/2009 | Roumeliotis |
| 2009/0189974 A1 | 7/2009 | Deering |
| 2009/0210596 A1 | 8/2009 | Furuya |
| 2010/0041378 A1 | 2/2010 | Aceves |
| 2010/0109918 A1 | 5/2010 | Liebermann |
| 2010/0110368 A1 | 5/2010 | Chaum |
| 2010/0179452 A1 | 7/2010 | Srinivasan |
| 2010/0182242 A1 | 7/2010 | Fields et al. |
| 2010/0182450 A1 | 7/2010 | Kumar |
| 2010/0198494 A1 | 8/2010 | Chao |
| 2010/0199232 A1 | 8/2010 | Mistry et al. |
| 2010/0241350 A1 | 9/2010 | Cioffi et al. |
| 2010/0245585 A1 | 9/2010 | Fisher et al. |
| 2010/0267276 A1 | 10/2010 | Wu |
| 2010/0292917 A1 | 11/2010 | Emam et al. |
| 2010/0298976 A1 | 11/2010 | Sugihara et al. |
| 2010/0305845 A1 | 12/2010 | Alexandre et al. |
| 2010/0308999 A1 | 12/2010 | Chornenky |
| 2011/0066383 A1 | 3/2011 | Jangle |
| 2011/0071830 A1 | 3/2011 | Kim |
| 2011/0092249 A1 | 4/2011 | Evanitsky |
| 2011/0124383 A1 | 5/2011 | Garra et al. |
| 2011/0125735 A1 | 5/2011 | Petrou |
| 2011/0181422 A1 | 7/2011 | Tran |
| 2011/0187640 A1 | 8/2011 | Jacobsen |
| 2011/0211760 A1 | 9/2011 | Boncyk |
| 2011/0216006 A1 | 9/2011 | Litschel |
| 2011/0221670 A1 | 9/2011 | King, III et al. |
| 2011/0246064 A1 | 10/2011 | Nicholson |
| 2011/0260681 A1 | 10/2011 | Guccione |
| 2011/0307172 A1 | 12/2011 | Jadhav et al. |
| 2012/0016578 A1 | 1/2012 | Coppens |
| 2012/0053826 A1 | 3/2012 | Slamka |
| 2012/0062357 A1 | 3/2012 | Slamka |
| 2012/0069511 A1 | 3/2012 | Azera |
| 2012/0075168 A1 | 3/2012 | Osterhout et al. |
| 2012/0082962 A1 | 4/2012 | Schmidt |
| 2012/0085377 A1 | 4/2012 | Trout |
| 2012/0092161 A1 | 4/2012 | West |
| 2012/0092460 A1 | 4/2012 | Mahoney |
| 2012/0123784 A1 | 5/2012 | Baker et al. |
| 2012/0136666 A1 | 5/2012 | Corpier et al. |
| 2012/0143495 A1 | 6/2012 | Dantu |
| 2012/0162423 A1 | 6/2012 | Xiao et al. |
| 2012/0194552 A1 | 8/2012 | Osterhout et al. |
| 2012/0206335 A1 | 8/2012 | Osterhout et al. |
| 2012/0206607 A1 | 8/2012 | Morioka |
| 2012/0207356 A1 | 8/2012 | Murphy |
| 2012/0214418 A1 | 8/2012 | Lee |
| 2012/0220234 A1 * | 8/2012 | Abreu | G02C 3/003 |
| | | | 455/41.2 |
| 2012/0232430 A1 | 9/2012 | Boissy et al. |
| 2012/0249797 A1 | 10/2012 | Haddick et al. |
| 2012/0252483 A1 | 10/2012 | Farmer et al. |
| 2012/0316884 A1 | 12/2012 | Rozaieski et al. |
| 2012/0323485 A1 | 12/2012 | Mutoh |
| 2012/0327194 A1 | 12/2012 | Shiratori |
| 2013/0002452 A1 | 1/2013 | Lauren |
| 2013/0044005 A1 | 2/2013 | Foshee et al. |
| 2013/0046541 A1 | 2/2013 | Klein et al. |
| 2013/0066636 A1 | 3/2013 | Singhal |
| 2013/0079061 A1 | 3/2013 | Jadhav |
| 2013/0090133 A1 | 4/2013 | D'Jesus Bencci |
| 2013/0115578 A1 | 5/2013 | Shiina |
| 2013/0115579 A1 | 5/2013 | Taghavi |
| 2013/0116559 A1 | 5/2013 | Levin |
| 2013/0127980 A1 | 5/2013 | Haddick |
| 2013/0128051 A1 | 5/2013 | Velipasalar et al. |
| 2013/0131985 A1 | 5/2013 | Weiland et al. |
| 2013/0141576 A1 | 6/2013 | Lord et al. |
| 2013/0144629 A1 | 6/2013 | Johnston |
| 2013/0155474 A1 | 6/2013 | Roach et al. |
| 2013/0157230 A1 | 6/2013 | Morgan |
| 2013/0184982 A1 | 7/2013 | DeLuca |
| 2013/0201344 A1 | 8/2013 | Sweet, III |
| 2013/0204605 A1 | 8/2013 | Illgner-Fehns |
| 2013/0211718 A1 | 8/2013 | Yoo et al. |

(56) References Cited

U.S. PATENT DOCUMENTS

| | | |
|---|---|---|
| 2013/0218456 A1 | 8/2013 | Zelek et al. |
| 2013/0202274 A1 | 9/2013 | Chan |
| 2013/0228615 A1 | 9/2013 | Gates et al. |
| 2013/0229669 A1 | 9/2013 | Smits |
| 2013/0243250 A1 | 9/2013 | France |
| 2013/0245396 A1 | 9/2013 | Berman et al. |
| 2013/0250078 A1 | 9/2013 | Levy |
| 2013/0250233 A1 | 9/2013 | Blum et al. |
| 2013/0253818 A1 | 9/2013 | Sanders et al. |
| 2013/0265450 A1 | 10/2013 | Barnes, Jr. |
| 2013/0271584 A1 | 10/2013 | Wexler et al. |
| 2013/0290909 A1 | 10/2013 | Gray |
| 2013/0307842 A1 | 11/2013 | Grinberg et al. |
| 2013/0311179 A1 | 11/2013 | Wagner |
| 2013/0328683 A1 | 12/2013 | Sitbon et al. |
| 2013/0332452 A1 | 12/2013 | Jarvis |
| 2014/0009561 A1 | 1/2014 | Sutherland |
| 2014/0031081 A1 | 1/2014 | Vossoughi |
| 2014/0031977 A1 | 1/2014 | Goldenberg et al. |
| 2014/0032596 A1 | 1/2014 | Fish et al. |
| 2014/0037149 A1 | 2/2014 | Zetune |
| 2014/0071234 A1 | 3/2014 | Millett |
| 2014/0081631 A1 | 3/2014 | Zhu et al. |
| 2014/0085446 A1 | 3/2014 | Hicks |
| 2014/0098018 A1 | 4/2014 | Kim et al. |
| 2014/0100773 A1 | 4/2014 | Cunningham et al. |
| 2014/0125700 A1 | 5/2014 | Ramachandran |
| 2014/0132388 A1 | 5/2014 | Alalawi |
| 2014/0133290 A1 | 5/2014 | Yokoo |
| 2014/0164994 A1* | 6/2014 | Myslinski ............... G06F 1/163 715/808 |
| 2014/0184384 A1 | 7/2014 | Zhu et al. |
| 2014/0204245 A1 | 7/2014 | Wexler |
| 2014/0222023 A1 | 8/2014 | Kim et al. |
| 2014/0233859 A1 | 8/2014 | Cho |
| 2014/0236932 A1 | 8/2014 | Ikonomov |
| 2014/0249847 A1 | 9/2014 | Soon-Shiong |
| 2014/0251396 A1 | 9/2014 | Subhashrao et al. |
| 2014/0253702 A1 | 9/2014 | Wexler |
| 2014/0278070 A1 | 9/2014 | McGavran |
| 2014/0281943 A1 | 9/2014 | Prilepov |
| 2014/0287382 A1 | 9/2014 | Villar Cloquell |
| 2014/0309806 A1 | 10/2014 | Ricci |
| 2014/0313040 A1 | 10/2014 | Wright, Sr. |
| 2014/0335893 A1 | 11/2014 | Ronen |
| 2014/0337621 A1* | 11/2014 | Nakhimov ............... G06F 1/163 713/168 |
| 2014/0343846 A1 | 11/2014 | Goldman et al. |
| 2014/0345956 A1 | 11/2014 | Kojina |
| 2014/0347265 A1 | 11/2014 | Aimone |
| 2014/0368412 A1 | 12/2014 | Jacobsen |
| 2014/0369541 A1 | 12/2014 | Miskin |
| 2014/0379336 A1 | 12/2014 | Bhatnager |
| 2015/0002808 A1 | 1/2015 | Rizzo, III et al. |
| 2015/0016035 A1 | 1/2015 | Tussy |
| 2015/0063661 A1 | 3/2015 | Lee |
| 2015/0081884 A1 | 3/2015 | Maguire |
| 2015/0099946 A1 | 4/2015 | Sahin |
| 2015/0109107 A1 | 4/2015 | Gomez et al. |
| 2015/0120186 A1 | 4/2015 | Heikes |
| 2015/0135310 A1* | 5/2015 | Lee ............... A61B 5/681 726/20 |
| 2015/0141085 A1 | 5/2015 | Nuovo et al. |
| 2015/0142891 A1 | 5/2015 | Haque |
| 2015/0154643 A1 | 6/2015 | Artman et al. |
| 2015/0125831 A1 | 7/2015 | Chandrashekhar Nair et al. |
| 2015/0196101 A1* | 7/2015 | Dayal ............... G01C 21/206 63/1.11 |
| 2015/0198454 A1* | 7/2015 | Moore ............... G06F 3/167 701/428 |
| 2015/0198455 A1* | 7/2015 | Chen ............... G01C 21/3629 701/428 |
| 2015/0199566 A1* | 7/2015 | Moore ............... G06K 9/00442 348/47 |
| 2015/0201181 A1* | 7/2015 | Moore ............... H04N 13/0239 348/47 |
| 2015/0211858 A1 | 7/2015 | Jerauld |
| 2015/0219757 A1 | 8/2015 | Boelter et al. |
| 2015/0223355 A1* | 8/2015 | Fleck ............... H05K 5/026 361/679.03 |
| 2015/0253886 A1* | 9/2015 | Wei ............... G06F 3/041 345/173 |
| 2015/0256977 A1 | 9/2015 | Huang |
| 2015/0257555 A1 | 9/2015 | Wong |
| 2015/0260474 A1 | 9/2015 | Rublowsky |
| 2015/0262509 A1 | 9/2015 | Labbe |
| 2015/0279172 A1 | 10/2015 | Hyde |
| 2015/0330787 A1 | 11/2015 | Cioffi et al. |
| 2015/0336276 A1 | 11/2015 | Song |
| 2015/0341591 A1 | 11/2015 | Kelder et al. |
| 2015/0346496 A1 | 12/2015 | Haddick et al. |
| 2015/0356345 A1 | 12/2015 | Velozo |
| 2015/0356837 A1 | 12/2015 | Pajestka |
| 2015/0358450 A1* | 12/2015 | Ushakov ............... H04B 1/385 455/575.2 |
| 2015/0364943 A1 | 12/2015 | Vick |
| 2015/0367176 A1 | 12/2015 | Bejestan |
| 2015/0375395 A1 | 12/2015 | Kwon |
| 2016/0007158 A1 | 1/2016 | Venkatraman |
| 2016/0028917 A1 | 1/2016 | Wexler |
| 2016/0042228 A1 | 2/2016 | Opalka |
| 2016/0078289 A1 | 3/2016 | Michel |
| 2016/0098138 A1* | 4/2016 | Park ............... G06F 3/0416 345/173 |
| 2016/0156850 A1 | 6/2016 | Werblin et al. |
| 2016/0198319 A1 | 7/2016 | Huang |
| 2016/0227009 A1* | 8/2016 | Kim ............... B60K 35/00 |
| 2016/0350514 A1 | 12/2016 | Rajendran |

FOREIGN PATENT DOCUMENTS

| | | |
|---|---|---|
| CN | 201440733 | 4/2010 |
| CN | 101803988 | 8/2010 |
| CN | 101647745 | 1/2011 |
| CN | 102316193 | 1/2012 |
| CN | 102631280 | 8/2012 |
| CN | 202547659 | 11/2012 |
| CN | 202722736 | 2/2013 |
| CN | 102323819 | 6/2013 |
| CN | 103445920 | 12/2013 |
| DE | 102011080056 | 1/2013 |
| DE | 102012000587 | 7/2013 |
| DE | 102012202614 | 8/2013 |
| EP | 1174049 | 9/2004 |
| EP | 1721237 | 11/2006 |
| EP | 236855 | 9/2011 |
| EP | 2371339 | 10/2011 |
| EP | 2127033 | 8/2012 |
| EP | 2581856 | 4/2013 |
| EP | 2751775 | 7/2016 |
| FR | 2885251 | 11/2006 |
| GB | 2401752 | 11/2004 |
| JP | 1069539 | 3/1998 |
| JP | 2001304908 | 10/2001 |
| JP | 2010012529 | 1/2010 |
| JP | 2010182193 | 8/2010 |
| JP | 4727352 | 7/2011 |
| JP | 2013169611 | 9/2013 |
| KR | 100405636 | 11/2003 |
| KR | 20080080688 | 9/2008 |
| KR | 20120020212 | 3/2012 |
| KR | 1250929 | 4/2013 |
| WO | WO1995004440 | 2/1995 |
| WO | WO 9949656 | 9/1999 |
| WO | WO 0010073 | 2/2000 |
| WO | WO 0038393 | 6/2000 |
| WO | WO 179956 | 10/2001 |
| WO | WO 2004/076974 | 9/2004 |
| WO | WO 2005083546 A1 * | 9/2005 ........... A44C 5/0007 |
| WO | WO 2006/028354 | 3/2006 |
| WO | WO 2006/045819 | 5/2006 |
| WO | WO 2007/031782 | 3/2007 |

(56) References Cited

FOREIGN PATENT DOCUMENTS

| WO | WO 2008/008791 | 1/2008 | | |
|---|---|---|---|---|
| WO | WO 2008015375 | 2/2008 | | |
| WO | WO 2008035993 | 3/2008 | | |
| WO | WO 2008/096134 | 8/2008 | | |
| WO | WO2008127316 | 10/2008 | | |
| WO | WO 2010/062481 | 6/2010 | | |
| WO | WO 2010/109313 | 9/2010 | | |
| WO | WO 2012/040703 | 3/2012 | | |
| WO | WO2012163675 | 12/2012 | | |
| WO | WO 2013/045557 | 4/2013 | | |
| WO | WO 2013/054257 | 4/2013 | | |
| WO | WO 2013/067539 | 5/2013 | | |
| WO | WO 2013/147704 | 10/2013 | | |
| WO | WO 2014104531 | 7/2014 | | |
| WO | WO 2014/138123 | 9/2014 | | |
| WO | WO 2014172378 | 10/2014 | | |
| WO | WO 2015037912 A1 * | 3/2015 | ............ | G06F 1/163 |
| WO | WO 2015065418 | 5/2015 | | |
| WO | WO2015092533 | 6/2015 | | |
| WO | WO 2015108882 | 7/2015 | | |
| WO | WO2015127062 | 8/2015 | | |

OTHER PUBLICATIONS

Cardonha et al.; "A Crowdsourcing Platform for the Construction of Accessibility Maps"; W4A'13 Proceedings of the 10$^{th}$ International Cross-Disciplinary Conference on Web Accessibility; Article No. 26; 2013; 5 pages.

Bujacz et al.; "Remote Guidance for the Blind—A Proposed Teleassistance System and Navigation Trials"; Conference on Human System Interactions; May 25-27, 2008; 6 pages.

Rodriguez et al; "CrowdSight: Rapidly Prototyping Intelligent Visual Processing Apps"; AAAI Human Computation Workshop (HCOMP); 2011; 6 pages.

Chaudary et al.; "Alternative Navigation Assistance Aids for Visually Impaired Blind Persons"; Proceedings of ICEAPVI; Feb. 12-14, 2015; 5 pages.

Garaj et al.; "A System for Remote Sighted Guidance of Visually Impaired Pedestrians"; The British Journal of Visual Impairment; vol. 21, No. 2, 2003; 9 pages.

Coughlan et al.; "Crosswatch: A System for Providing Guidance to Visually Impaired Travelers at Traffic Intersections"; Journal of Assistive Technologies 7.2; 2013; 17 pages.

Sudol et al.; "LookTel—A Comprehensive Platform for Computer-Aided Visual Assistance"; Computer Vision and Pattern Recognition Workshops (CVPRW), 2010 IEEE Computer Society Conference; Jun. 13-18, 2010; 8 pages.

Paladugu et al.; "GoingEasy® with Crowdsourcing in the Web 2.0 World for Visually Impaired Users: Design and User Study"; Arizona State University; 8 pages.

Kammoun et al.; "Towards a Geographic Information System Facilitating Navigation of Visually Impaired Users"; Springer Berlin Heidelberg; 2012; 8 pages.

Bigham et al.; "VizWiz: Nearly Real-Time Answers to Visual Questions" Proceedings of the 23nd annual ACM symposium on User interface software and technology; 2010; 2 pages.

Guy et al; "CrossingGuard: Exploring Information Content in Navigation Aids for Visually Pedestrians" Proceedings of the SIGCHI Conference on Human Factors in Computing Systems; May 5-10, 2012; 10 pages.

Zhang et al.; "A Multiple Sensor-Based Shoe-Mounted User Interface Designed for Navigation Systems for the Visually Impaired"; 5$^{th}$ Annual ICST Wireless Internet Conference (WICON); Mar. 1-3, 2010; 9 pages.

Shoval et al.; "Navbelt and the Guidecane—Robotics-Based Obstacle-Avoidance Systems for the Blind and Visually Impaired"; IEEE Robotics & Automation Magazine, vol. 10, Issue 1; Mar. 2003; 12 pages.

Dowling et al.; "Intelligent Image Processing Constraints for Blind Mobility Facilitated Through Artificial Vision"; 8$^{th}$ Australian and NewZealand Intelligent Information Systems Conference (ANZIIS); Dec. 10-12, 2003; 7 pages.

Heyes, Tony; "The Sonic Pathfinder an Electronic Travel Aid for the Vision Impaired"; http://members.optuszoo.com.au/aheyew40/pa/pf_blerf.html; Dec. 11, 2014; 7 pages.

Lee et al.; "Adaptive Power Control of Obstacle Avoidance System Using Via Motion Context for Visually Impaired Person." International Conference on Cloud Computing and Social Networking (ICCCSN), Apr. 26-27, 2012 4 pages.

Wilson, Jeff, et al. "Swan: System for Wearable Audio Navigation"; 11th IEEE International Symposium on Wearable Computers; Oct. 11-13, 2007; 8 pages.

Borenstein et al.; "The GuideCane—A Computerized Travel Aid for the Active Guidance of Blind Pedestrians"; IEEE International Conference on Robotics and Automation; Apr. 21-27, 1997; 6 pages.

Bhatlawande et al.; "Way-finding Electronic Bracelet for Visually Impaired People"; IEEE Point-of-Care Healthcare Technologies (PHT), Jan. 16-18, 2013; 4 pages.

Blenkhorn et al.; "An Ultrasonic Mobility Device with Minimal Audio Feedback"; Center on Disabilities Technology and Persons with Disabilities Conference; Nov. 22, 1997; 5 pages.

Mann et al.; "Blind Navigation with a Wearable Range Camera and Vibrotactile Helmet"; 19$^{th}$ ACM International Conference on Multimedia; Nov. 28, 2011; 4 pages.

Shoval et al.; "The Navbelt—A Computerized Travel Aid for the Blind"; RESNA Conference, Jun. 12-17, 1993; 6 pages.

Kumar et al.; "An Electronic Travel Aid for Navigation of Visually Impaired Persons"; Communications Systems and Networks (COMSNETS), 2011 Third International Conference; Jan. 2011; 5 pages.

Pawar et al.; "Multitasking Stick for Indicating Safe Path to Visually Disable People"; IOSR Journal of Electronics and Communication Engineering (IOSR-JECE), vol. 10, Issue 3, Ver. II; May-Jun 2015; 5 pages.

Pagliarini et al.; "Robotic Art for Wearable"; Proceedings of EUROSIAM: European Conference for the Applied Mathematics and Informatics 2010; 10 pages.

Greenberg et al.; "Finding Your Way: A Curriculum for Teaching and Using the Braillenote with Sendero GPS 2011"; California School for the Blind; 2011; 190 pages.

Helal et al.; "Drishti: An Integrated Navigation System for Visually Impaired and Disabled"; Fifth International Symposium on Wearable Computers; Oct. 8-9, 2001; 8 pages.

Parkes, Don; "Audio Tactile Systems for Designing and Learning Complex Environments as a Vision Impaired Person: Static and Dynamic Spatial Information Access"; EdTech-94 Proceedings; 1994; 8 pages.

Zeng et al.; "Audio-Haptic Browser for a Geographical Information System"; ICCHP 2010, Part II, LNCS 6180; Jul. 14-16, 2010; 8 pages.

AlZuhair et al.; "NFC Based Applications for Visually Impaired People—A Review"; IEEE International Conference on Multimedia and Expo Workshops (ICMEW), Jul. 14, 2014; 7 pages.

Graf, Christian; "Verbally Annotated Tactile Maps—Challenges and Approaches"; Spatial Cognition VII, vol. 6222; Aug. 15-19, 2010; 16 pages.

Hamid, Nazatul Naquiah Abd; "Facilitating Route Learning Using Interactive Audio-Tactile Maps for Blind and Visually Impaired People"; CHI 2013 Extended Abstracts; Apr. 27, 2013; 6 pages.

Ramya, et al.; "Voice Assisted Embedded Navigation System for the Visually Impaired"; International Journal of Computer Applications; vol. 64, No. 13, Feb. 2013; 7 pages.

Caperna et al.; "A Navigation and Object Location Device for the Blind"; Tech. rep. University of Maryland College Park; May 2009; 129 pages.

Burbey et al.; "Human Information Processing with the Personal Memex"; ISE 5604 Fall 2005; Dec. 6, 2005; 88 pages.

Ghiani, et al.; "Vibrotactile Feedback to Aid Blind Users of Mobile Guides"; Journal of Visual Languages and Computing 20; 2009; 13 pages.

Guerrero et al.; "An Indoor Navigation System for the Visually Impaired"; Sensors vol. 12, Issue 6; Jun. 13, 2012; 23 pages.

(56) References Cited

OTHER PUBLICATIONS

Nordin et al.; "*Indoor Navigation and Localization for Visually Impaired People Using Weighted Topological Map*"; Journal of Computer Science vol. 5, Issue 11; 2009; 7 pages.
Hesch et al.; "*Design and Analysis of a Portable Indoor Localization Aid for the Visually Impaired*"; International Journal of Robotics Research; vol. 29; Issue 11; Sep. 2010; 15 pgs.
Joseph et al.; "*Visual Semantic Parameterization—To Enhance Blind User Perception for Indoor Navigation*"; Multimedia and Expo Workshops (ICMEW), 2013 IEEE International Conference; Jul. 15, 2013; 7 pages.
Katz et al; "*NAVIG: Augmented Reality Guidance System for the Visually Impaired*"; Virtual Reality (2012) vol. 16; 2012; 17 pages.
Rodríguez et al.; "*Assisting the Visually Impaired: Obstacle Detection and Warning System by Acoustic Feedback*"; Sensors 2012; vol. 12; 21 pages.
Treuillet; "*Outdoor/Indoor Vision-Based Localization for Blind Pedestrian Navigation Assistance*"; WSPC/Instruction File; May 23, 2010; 16 pages.
Ran et al.; "*Drishti: An Integrated Indoor/Outdoor Blind Navigation System and Service*"; Proceeding PERCOM '04 Proceedings of the Second IEEE International Conference on Pervasive Computing and Communications (PerCom'04); 2004; 9 pages.
Wang, et al.; "*Camera-Based Signage Detection and Recognition for Blind Persons*"; $13^{th}$ International Conference (ICCHP) Part 2 Proceedings; Jul. 11-13, 2012; 9 pages.
Krishna et al.; "*A Systematic Requirements Analysis and Development of an Assistive Device to Enhance the Social Interaction of People Who are Blind or Visually Impaired*"; Workshop on Computer Vision Applications for the Visually Impaired; Marseille, France; 2008; 12 pages.
Lee et al.; "*A Walking Guidance System for the Visually Impaired*"; International Journal of Pattern Recognition and Artificial Intelligence; vol. 22; No. 6; 2008; 16 pages.
Ward et al.; "*Visual Experiences in the Blind Induced by an Auditory Sensory Substitution Device*"; Journal of Consciousness and Cognition; Oct. 2009; 30 pages.
Merino-Garcia, et al.; "*A Head-Mounted Device for Recognizing Text in Natural Sciences*"; CBDAR'11 Proceedings of the $4^{th}$ International Conference on Camera-Based Document Analysis and Recognition; Sep. 22, 2011; 7 pages.
Yi, Chucai; "*Assistive Text Reading from Complex Background for Blind Persons*"; CBDAR'11 Proceedings of the $4^{th}$ International Conference on Camera-Based Document Analysis and Recognition; Sep. 22, 2011; 7 pages.
Yang, et al.; "*Towards Automatic Sign Translation*"; The Interactive Systems Lab, Carnegie Mellon University; 2001; 5 pages.
Meijer, Dr. Peter B.L.; "*Mobile OCR, Face and Object Recognition for the Blind*"; The vOICe, www.seeingwithsound.com/ocr.htm; Apr. 18, 2014; 7 pages.
Omron; Optical Character Recognition Sensor User's Manual; 2012; 450 pages.
Park, Sungwoo; "*Voice Stick*"; www.yankodesign.com/2008/08/21/voice-stick; Aug. 21, 2008; 4 pages.
Rentschler et al.; "*Intelligent Walkers for the Elderly: Performance and Safety Testing of VA-PAMAID Robotic Walker*"; Department of Veterans Affairs Journal of Rehabilitation Research and Development; vol. 40, No. 5; Sep./Oct. 2013; 9pages.
Science Daily; "*Intelligent Walker Designed to Assist the Elderly and People Undergoing Medical Rehabilitation*"; http://www.sciencedaily.com/releases/2008/11/081107072015.htm; Jul. 22, 2014; 4 pages.
Glover et al.; "*A Robotically-Augmented Walker for Older Adults*"; Carnegie Mellon University, School of Computer Science; Aug. 1, 2003; 13 pages.
OrCam; www.orcam.com; Jul. 22, 2014; 3 pages.
Eccles, Lisa; "*Smart Walker Detects Obstacles*"; Electronic Design; http://electronicdesign.com/electromechanical/smart-walker-detects-obstacles; Aug. 20, 2001; 2 pages.

Graft, Birgit; "*An Adaptive Guidance System for Robotic Walking Aids*"; Journal of Computing and Information Technology—CIT 17; 2009; 12 pages.
Frizera et al.; "*The Smart Walkers as Geriatric Assistive Device. The SIMBIOSIS Purpose*"; Gerontechnology, vol. 7, No. 2; Jan. 30, 2008; 6 pages.
Rodriquez-Losada et al.; "*Guido, The Robotic Smart Walker for the Frail Visually Impaired*"; IEEE International Conference on Robotics and Automation (ICRA); Apr. 18-22, 2005; 15 pages.
Kayama et al.; "*Outdoor Environment Recognition and Semi-Autonomous Mobile Vehicle for Supporting Mobility of the Elderly and Disabled People*"; National Institute of Information and Communications Technology, vol. 54, No. 3; Aug. 2007; 11 pages.
Kalra et al.; "*A Braille Writing Tutor to Combat Illiteracy in Developing Communities*"; Carnegie Mellon University Research Showcase, Robotics Institute; 2007; 10 pages.
Blaze Engineering; "*Visually Impaired Resource Guide: Assistive Technology for Students who use Braille*"; Braille 'n Speak Manual; http://www.blaize.com; Nov. 17, 2014; 5 pages.
AppleVis; *An Introduction to Braille Screen Input on iOS 8*; http://www.applevis.com/guides/braille-ios/introduction-braille-screen-input-ios-8, Nov. 16, 2014; 7 pages.
Dias et al.; "*Enhancing an Automated Braille Writing Tutor*"; IEEE/RSJ International Conference on Intelligent Robots and Systems; Oct. 11-15, 2009; 7 pages.
D'Andrea, Frances Mary; "*More than a Perkins Brailler: A Review of the Mountbatten Brailler, Part I*"; AFB AccessWorld Magazine; vol. 6, No. 1, Jan. 2005; 9 pages.
Trinh et al.; "*Phoneme-based Predictive Text Entry Interface*"; Proceedings of the 16th International ACM SIGACCESS Conference on Computers & Accessibility; Oct. 2014; 2 pgs.
Merri et al.; "*The Instruments for a Blind Teacher of English: The challenge of the board*"; European Journal of Psychology of Education, vol. 20, No. 4 (Dec. 2005), 15 pages.
Kirinic et al.; "*Computers in Education of Children with Intellectual and Related Developmental Disorders*"; International Journal of Emerging Technologies in Learning, vol. 5, 2010, 5 pages.
Campos et al.; "*Design and Evaluation of a Spoken-Feedback Keyboard*"; Department of Information Systems and Computer Science, INESC-ID/IST/Universidade Tecnica de Lisboa, Jul. 2004; 6 pages.
Ebay; Matin (Made in Korea) Neoprene Canon DSLR Camera Curved Neck Strap #6782; http://www.ebay.com/itm/MATIN-Made-in-Korea-Neoprene-Canon-DSLR-Camera-Curved-Neck-Strap-6782-/281608526018?hash=item41912d18c2:g:~pMAAOSwe-FU6zDa ; 4 pages.
Newegg; Motorola S10-HD Bluetooth Stereo Headphone w/ Comfortable Sweat Proof Design; http://www.newegg.com/Product/Product.aspx?Item=9SIA0NW2G39901&Tpk=9sia0nw2g39901; 4 pages.
Newegg; Motorola Behind the Neck Stereo Bluetooth Headphone Black/Red Bulk (S9)—OEM; http://www.newegg.com/Product/Product.aspx?Item=N82E16875982212&Tpk=n82e16875982212; 3 pages.
Wu et al. "Fusing Multi-Modal Features for Gesture Recognition", Proceedings of the $15^{th}$ ACM on International Conference on Multimodal Interaction, Dec. 9, 2013, ACM, pp. 453-459.
Pitsikalis et al. "Multimodal Gesture Recognition via Multiple Hypotheses Rescoring", Journal of Machine Learning Research, Feb. 2015, pp. 255-284.
Shen et al. "Walkie-Markie: Indoor Pathway Mapping Made Easy" $10^{th}$ USENIX Symposium on Networked Systems Design and Implementation (NSDI'13); pp. 85-98, 2013.
Tu et al. "Crowdsourced Routing II D2.6" 34 pages; 2012.
De Choudhury et al. "Automatic Construction of Travel Itineraries Using Social Breadcrumbs" pp. 35-44; Jun. 2010.
Zhang, Shanjun; Yoshino, Kazuyoshi; A Braille Recognition System by the Mobile Phone with Embedded Camera; 2007; IEEE.
Diallo, Amadou; Sep. 18, 2014; Apple iOS8: Top New Features, Forbes Magazine.

(56) References Cited

OTHER PUBLICATIONS

N. Kalar, T. Lawers, D. Dewey, T. Stepleton, M.B. Dias; Iterative Design of a Braille Writing Tutor to Combat Illiteracy; Aug. 30, 2007; IEEE.

Bharathi et al.; "Effective Navigation for Visually Impaired by Wearable Obstacle Avoidance System;" 2012 International Conference on Computing, Electronics and Electrical Technologies (ICCEET); pp. 956-958; 2012.

Pawar et al.; "Review Paper on Multitasking Stick for Guiding Safe Path for Visually Disable People;" IJPRET; vol. 3, No. 9; pp. 929-936; 2015.

Ram et al.; "The People Sensor: A Mobility Aid for the Visually Impaired;" 2012 16th International Symposium on Wearable Computers; pp. 166-167; 2012.

Singhal; "The Development of an Intelligent Aid for Blind and Old People;" Emerging Trends and Applications in Computer Science (ICETACS), 2013 1st International Conference; pp. 182-185; Sep. 13, 2013.

Aggarwal et al.; "All-in-One Companion for Visually Impaired;" International Journal of Computer Applications; vol. 79, No. 14; pp. 37-40; Oct. 2013.

"Light Detector" EveryWare Technologies; 2 pages; Jun. 18, 2016.

Arati et al. "Object Recognition in Mobile Phone Application for Visually Impaired Users;" IOSR Journal of Computer Engineering (IOSR-JCE); vol. 17, No. 1; pp. 30-33.

Yabu et al.; "Development of a Wearable Ilaptic Tactile Interface as an Aid for the Hearing and/or Visually Impaired;" NTUT Education of Disabilities; vol. 13; pp. 5-12; 2015.

Mau et al.; "BlindAid: an Electronic Travel Aid for the Blind;" The Robotics Institute Carnegie Mellon University; 27 pages; May 2008.

Shidujaman et al.; "Design and navigation Prospective for Wireless Power Transmission Robot;" IEEE; Jun. 2015.

\* cited by examiner

| KIT | INCLUDED PODS | OPTIONAL PODS |
|---|---|---|
| EXCERCISE | ACCELEROMETER POD<br>HEALTH POD<br>MOTION POD | EMERGENCY DISPLAY POD |
| NAVIGATION | CAMERA POD<br>ACCELEROMETER POD<br>GPS POD<br>OUTPUT POD | BATTERY POD<br>EMERGENCY DISPLAY POD<br>TELEPRESENCE POD |
| BLIND USE | CAMERA POD<br>ACCELEROMETER POD<br>OUTPUT POD<br>TELEPRESENCE POD | BRAILLE POD<br>INPUT POD |
| SPORTING EVENTS | CAMERA POD<br>RECORDER POD<br>NETWORK COMMUNICATION POD<br>OUTPUT POD | USB POD |
| POLICE USE | MAIN UNIT HAVING<br>THIRD CONNECTOR<br>2 CAMERA PODS<br>RECORDER POD<br>OUTPUT POD | NETWORK COMMUNICATION POD<br>BATTERY POD<br>GPS POD |

FIG. 6

MODULAR SMART NECKLACE

BACKGROUND

Field

The present disclosure relates to a modular wearable device that can include various combinations of components for receiving input, detecting data, outputting data, power storage, wired communications, and wireless communications.

Description of the Related Art

Wearable smart devices have been introduced to the marketplace. These wearable smart devices can resemble glasses or other wearable articles and they typically include similar components to smart mobile telephones (smartphones), such as processing and memory components, input components, and output components. As with smartphones, wearable smart devices are typically provided in relatively few preassembled base packages having components preselected by the design team. When components of these wearable smart devices become obsolete and/or better technology becomes available, a user cannot simply swap the old component for a new component; rather, he or she must purchase an entirely new device that includes the new component. Many consumers thus do not upgrade to new wearable smart devices as new versions are provided, as the cost can be prohibitively or undesirably high. The consumers who do continue to upgrade to these new versions of wearable smart devices can be exposed to a significant economic strain due to the relatively high costs.

The components in wearable smart devices are typically integral to the wearable smart device such that replacement of particular components is relatively difficult at best. Accordingly, if a core component (i.e., a camera or speakers) becomes broken, a user cannot simply replace the broken component; rather, he must purchase a new wearable smart device to have an operating component.

The base price of wearable smart devices can be relatively high, at least partially because of inclusion of numerous components. Typical consumers do not use all of the provided components, so they are paying extra money for components that they will likely never use. For example, a blind person may find wearable smart devices advantageous; however, he may have no use for a visible display that added significant cost to the wearable smart device.

Thus, there is a need for customizable and easily repairable wearable smart devices.

SUMMARY

What is described is a modular smart necklace. The modular smart necklace includes a first pod having an outer casing, a proximate connector mechanically coupled to the outer casing, and a first component electrically coupled to the proximate connector. The first component can at least one of receive input data or output data. The modular smart necklace also includes a second pod having an outer casing, a proximate connector mechanically coupled to the outer casing, and a second component electrically coupled to the proximate connector. The second component can at least one of receive input data or output data. The modular smart necklace also includes a main unit having an outer casing having a curvature. The main unit also includes a first connector coupled to the outer casing and configured to be removably, pivotably and electrically coupled to the proximate connector of the first pod. The main unit also includes a second connector coupled to the outer casing and configured to be removably, pivotably and electrically coupled to the proximate connector of the second pod. The outer casing of the main unit can rest on a back of a neck and the outer casing of the first connector and the outer casing of the second connector can each rotate about a shoulder. The main unit also includes a battery for providing power to the first component and the second component. The main unit also includes a mobile processor electrically coupled to the first connector and the second connector. The mobile processor can receive the input data from at least one of the first pod or the second pod, determine output data based on the received input data, and output the output data via at least one of the first pod or the second pod.

Also described is a modular smart necklace having a camera pod having an outer casing, a distal connector mechanically coupled to the outer casing, a proximate connector mechanically coupled to the outer casing, and a camera electrically coupled to the proximate connector and for detecting image data. The modular smart necklace also includes an accelerometer pod having an outer casing, a distal connector mechanically coupled to the outer casing, a proximate connector mechanically coupled to the outer casing, and an accelerometer for detecting an acceleration. The modular smart necklace also includes an output pod having an outer casing, a distal connector mechanically coupled to the outer casing, a proximate connector mechanically coupled to the outer casing, and at least one of a speaker or a vibration unit for outputting data. The speaker or vibration unit is electrically coupled to the proximate connector. The proximate connector of one of the camera pod, the accelerometer pod, or the output pod is coupled to the distal connector of another of the camera pod, the accelerometer pod, or the output pod. The modular smart necklace also includes a main unit having an outer casing having a curvature. The main unit also includes a first connector coupled to the outer casing and configured to be removably, pivotably and electrically coupled to the proximate connector of one of the camera pod, the accelerometer pod, or the output pod. The main unit also includes a second connector coupled to the outer casing and configured to be removably, pivotably and electrically coupled to the proximate connector of one of the camera pod, the accelerometer pod, or the output pod. The outer casing of the main unit can rest on a back of a neck and the outer casing of each of the pods coupled to the first connector and the second connector can each rotate with a curve of a shoulder. The outer casing of the one of the camera pod, the accelerometer pod, or the output pod that is not directly coupled to the main unit can extend farther downwards across a chest or the shoulder than the two of the camera pod, the accelerometer pod, or the output pod that are directly coupled to the main unit. The main unit can also include a battery for providing power to the camera and the at least one of the speaker or the vibration unit and a non-transitory memory configured to store at least one of map data or object data. The main unit also includes a processor electrically coupled to the first connector and the second connector and configured to receive the detected image data and the detected acceleration, to determine output data based on the image data and the acceleration, and to instruct the at least one of the vibration unit or the speaker to output the output data.

Also described is a kit for use with a main unit of a modular smart necklace having a first connector, a second connector, and a processor. The kit includes a plurality of pods each having an outer casing, a distal connector, and proximate connector configured to be mechanically and electrically coupled to at least one of the first connector of the main unit or a distal connector of another pod. The kit can be a blind kit having a camera pod having a camera electrically coupled to the proximate connector and configured to detect image data and an accelerometer pod having an accelerometer electrically coupled to the proximate connector and configured to detect acceleration. The blind kit can also include an output pod having at least one of a speaker or a vibration unit electrically coupled to the proximate connector and configured to output data received from the processor of the main unit and a telepresence pod including at least one of a network access device or a pod processor electrically coupled to the proximate connector and configured to allow communication with a third party via the camera pod and the output pod. The kit can also be a navigation kit that includes the camera pod, the accelerometer pod, the output pod, and a GPS pod including a GPS unit electrically coupled to the proximate connector and configured to detect location data. The kit can also be an exercise kit having the accelerometer pod, a health pod having at least one of a heart rate sensor or a respiration sensor configured to detect a heart rate or a respiration rate. The exercise kit can also include a motion pod including a motion-to-power converter electrically coupled to the proximate connector and configured to convert motion power to electrical power. The kit can also include a sporting event kit having the output pod, the camera pod, and a network communication pod including a network access device electrically coupled to the proximate connector and configured to communicate with a second device via a network. The sporting event kit can also include a recorder pod including an input device configured to receive an input and a memory configured to store the image data in response to receiving the input.

BRIEF DESCRIPTION OF THE DRAWINGS

Other systems, methods, features, and advantages of the present invention will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale, and may be exaggerated to better illustrate the important features of the present invention. In the drawings, like reference numerals designate like parts throughout the different views, wherein:

FIG. 6 is a chart illustrating various kits that include pods for various purposes according to an embodiment of the present invention.

DETAILED DESCRIPTION

Disclosed herein are modular smart necklaces and methods of operation thereof. The smart necklaces provide several benefits and advantages such as the ability of a user to design a smart necklace having only desired components. This provides advantages such as reducing costs of the smart necklaces to end users so that more end users may be willing to purchase a smart necklace as well as the ability for a cost-conscious individual to create an affordable smart necklace having only components necessary to him. The smart necklaces provide the additional advantage of being modular so that existing components can be upgraded with new or better components. This is advantageous because new components can be sold as they become available rather than waiting for a new release of the entire wearable smart necklace, creating revenue from users who already have a smart necklace but wish to add the new, upgraded components. Because components are relatively easy to replace, the smart necklace has the additional advantage of quick and inexpensive repair, making the smart necklace more appealing to consumers. The smart necklace is also advantageous because it allows for various numbers of components to be added such that it can be designed to fit users having various body shapes and sizes.

An exemplary modular smart necklace includes a main unit having a battery or other power source, a memory, and a processor. The smart necklace also includes one or more pods that can be coupled to each other and to the main unit. The pods each include one or more components for providing particular functionality. For example, a camera pod can include a camera for detecting image data, a speaker pod can include a speaker for outputting audio data, and an alert pod can include a processor and network access device for alerting an emergency contact. The processor of the main unit can receive instructions from one or more pod (such as a pod having an input device), receive detected data from one or more pod (such as a pod having a sensor or a network access device), determine output data based on the instructions and the received data, and output the data using one or more pod (such as a pod having an output device). The main unit and each of the pods can include one or more connectors for mechanically and electrically connecting the components of the main unit and each of the pods together. The mechanical and electrical connections can be easily removable so that a user can change pods as he desires. When connected together, the main unit and the connected pods can resemble a necklace to be work about a user's neck.

Figure 1:
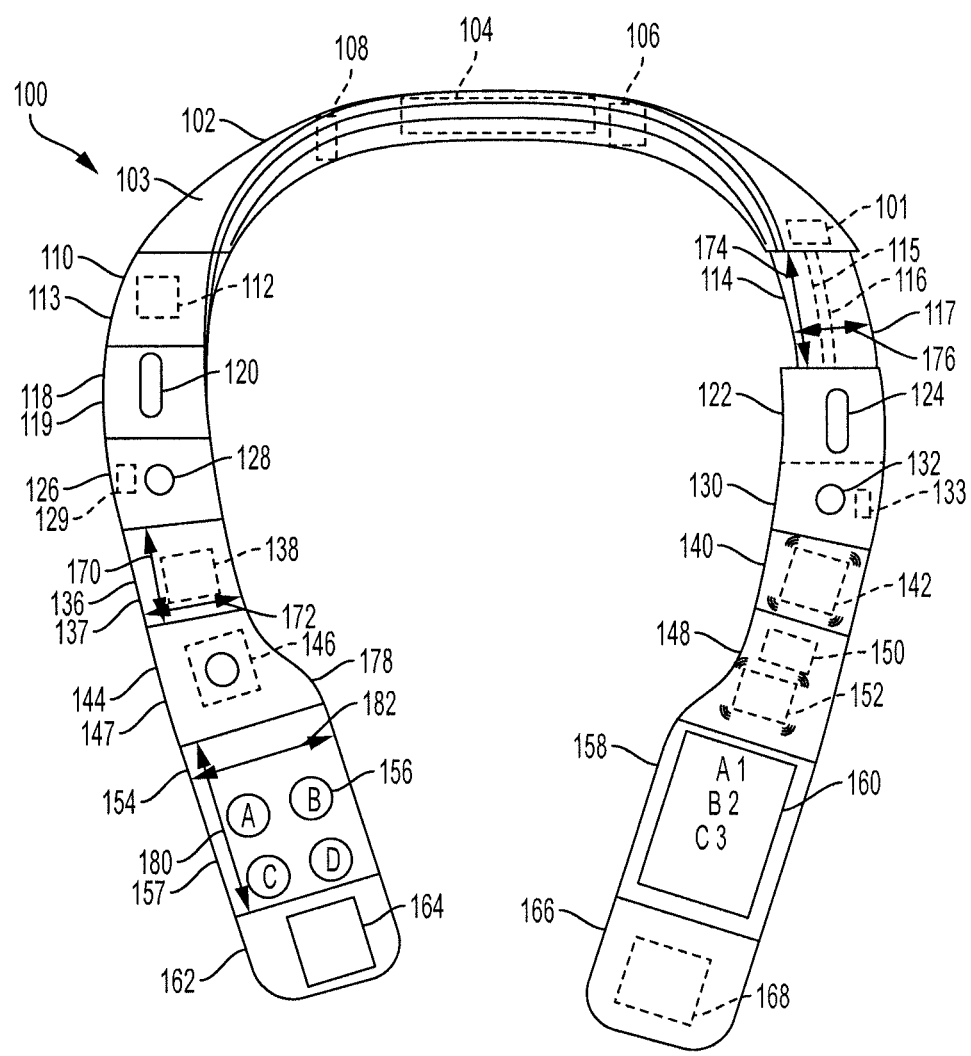
FIG. 1 illustrates a modular smart necklace having a main unit and a plurality of pods each having a component according to an embodiment of the present invention.

With reference now to FIG. 1, a modular smart necklace 100 may include a main unit 102 (or a main housing) and a plurality of pods (such as a vibration pod 110). The main unit 102 may include an outer casing 103 defining a cavity (not shown) and a mobile processor 106, a memory 108, a battery 104, and an input/output (I/O) port positioned within the cavity or elsewhere with respect to the main unit 102. The battery 104 may be a battery or other power storage device capable of storing power and providing it to the main unit 102 and/or one or more connected pods.

The mobile processor 106 may be a mobile computing processor such as an ARM processor, DSP processor, distributed processor, or other form of central processing. The mobile processor 106 may be designed to operate at lower voltages than a traditional processor to conserve power. The mobile processor 106 may also have a lower operating temperature than a traditional processor to prevent the modular smart necklace 100 from becoming undesirably hot.

The memory 108 may include one or any combination of the following: a RAM or other volatile or nonvolatile memory, a non-transitory memory or a data storage device, such as a hard disk drive, a solid state disk drive, a hybrid disk drive, or other appropriate data storage, and may further store machine-readable instructions, which may be loaded into the memory 108 and executed by the mobile processor 106.

The I/O port may include one or more ports for connecting to other devices and/or to peripherals, for example, directly or via a network. In some embodiments, the I/O port may additionally or instead be coupled to the battery 104 and receive power from a source (such as a USB port or a power converter) and provide the power to the battery 104. For example, the I/O port may include a headphone jack, a data port (such as a USB port), a wireless charging port, a Bluetooth or WiFi antenna, a radio frequency identification (RFID) antenna or reader, and/or a near field communication (NFC) unit.

The main unit 102 may be mechanically and electrically coupled to one or more pods, each having various features and functionalities. For example, a vibration (or output) pod 110 may include an outer casing 113 defining a cavity (not shown) and a vibration unit 112 positioned therein. The outer casing 113 of the vibration pod 110 may be removably coupled to the outer casing 103 of the main unit 102. For example, the outer casings 103, 113 may be coupled together via a removable connector (such as a snap connector). Additionally, the mechanical connection may be such that the outer casings 103, 113 can rotate or pivot relative to each other. The electrical connection allows data and/or power to be transferred between the battery 104, the mobile processor 106, and the memory 108 of the main unit 102 and the vibration unit 112 of the vibration pod 110.

The pods may also be coupled to other pods. For example, the vibration pod 110 may be mechanically and electrically coupled to another pod, such as a speaker pod 118 (another output pod). The speaker pod 118 (as with other pods) may include an outer casing 119 defining a cavity (not shown) and a speaker 120 positioned therein (other pods may include components other than a speaker). The outer casing 119 of the speaker pod 118 may be removably coupled to the outer casing 113 of the vibration pod 110. The outer casings 113, 119 may be rotatably and/or pivotably coupled or may be rigidly coupled. In some embodiments all of the pods are rotatably/pivotably coupled, in some embodiments all of the pods are rigidly coupled, and in some embodiments some pods may be rotatably/pivotably coupled and some pods may be rigidly coupled.

The modular smart necklace 100 may be created by connecting one or more pods to the main unit 102 and potentially coupling one or more pods together. The main unit 102 may have a curvature and be designed to rest on a back of a user's neck. The pods directly connected to the main unit 102 may pivot or rotate as they extend across the user's shoulders and additional pods may continue to pivot or rotate and follow the contours of the user's shoulders and chest.

Each of the pods can include various components and features. For example, vibration pod 110 includes the vibration unit 112 that includes a vibration motor or actuator capable of providing haptic and tactile output. In certain implementations, the vibration unit 112 may also be capable of producing sounds. The speaker 120 of the speaker pod 118 may be one or more speakers or other devices capable of producing sounds and/or vibrations. As disclosed above, the main unit 102 may be electrically connected to the vibration pod 110 and the vibration pod 110 may be electrically connected to the speaker pod 118. In that regard, the battery 104 of the main unit 102 may provide power to the vibration unit 112 and the speaker 120 and the mobile processor 106 may transmit and receive signals to/from the vibration unit 112 and the speaker 120.

The mobile processor 106 may communicate with the vibration unit 112 and the speaker 120 (along with components of other pods) using a pass-through communication protocol. For example, the protocol may include a controller area network (CAN bus) protocol. The mobile processor 106 may be capable of determining the capabilities of the components of each of the pods and controlling the components accordingly. In order to communicate with the components, the mobile processor 106 may assign a unique identifier to each of the connected pods and/or components and communicate with each of the pods by sending a message including the assigned identifiers to be received by the pod matching the identifier.

The modular smart necklace 100 may also include a spacer pod 114 that includes an outer casing 117. The spacer pod 114 may be electrically and mechanically coupled to the main unit 102 and to a second speaker pod 122. The connection may be removable and pivotable or rotatable. In some embodiments, the outer casing 117 of the spacer pod 114 may be flexible such that it can bend to better follow contours of a user's body.

The spacer pod 114 may include a data line 115 and a power line 116, each of which may include one or more wires or cables. The data line 115 may carry signals between components of other pods (such as a speaker 124 of the second speaker pod 122) and the mobile processor 106. The power line 116 may carry power signals between components of other pods (such as the speaker 124 of the second speaker pod 122) and the battery 104.

The spacer pod 114 may be positioned between any two pods or between a pod and the main unit 102. Accordingly, one or more spacer pods can be attached in order to change the physical layout of the modular smart necklace 100 to better fit people of various sizes and shapes. For example, if a user has relatively large shoulders, one or more spacer pods 114 may be coupled between the main unit 102 and additional pods, allowing a better fit for the user as well as allowing component pods (i.e., pods having components in addition to data and power lines) to be connected at the front of the user's body instead of on the user's shoulders. Positioning component pods at the front of the user's body may be desirable as it may allow components (such as a camera) to face forward instead of upward.

The second speaker pod 122 includes the second speaker 124. When the mobile processor 106 detects the speakers 120, 124, it may recognize that it can output stereo audio data instead of mono audio data. The number of pods that can be attached to the main unit 102 is unlimited; therefore, additional speaker pods can be added to provide surround sound.

The modular smart necklace 100 may also include a camera pod 126 and a camera pod 130, each having similar features. The camera pod 126 may include a camera 128 and a processor 129 and the camera pod 130 may include a camera 132 and a pod processor 133. One or both of the cameras 128, 132 may include a camera or other optical sensor capable of detecting image data. As with the speakers 120, 124, the mobile processor 106 may recognize that it can combine the image data received from the cameras 128, 132 to form stereo image data. The stereo image data can then be used to determine distance information corresponding to objects that are in the field of view of the cameras 128, 132. In another aspect, the cameras 128, 132 may be coupled to an actuator or motor (not shown) controllable by the mobile processor 106 and/or the pod processor 133 so that the positioning of the cameras 128, 132 can be controlled. This allows the mobile processor 106 to change a focal distance of the cameras 128, 132. Additional cameras can be added to improve the field of view and/or to improve the accuracy of distance information. For example, various cameras can be added being focused in different directions, increasing a field of view of the collection of cameras. As another example, three cameras may be included on a necklace for a blind user so that the necklace can provide detailed distance information for the blind user.

The camera pod 126 has the camera 128 and the processor 129. In some embodiments, a camera pod, or any other pod, can have more than one sensor. For example, one pod may include a camera and an infrared (IR) sensor, another may include a GPS chip, an accelerometer, and a gyroscope. The combination pods do not necessarily have to include related components. For example, a pod may include a camera and a speaker, or a camera and an accelerometer. These combination pods, like the other pods, may or may not include a processor, memory, or any other devices described herein.

The modular smart necklace 100 may also include a global positioning system (GPS) pod 136 including a GPS unit 138. The GPS unit 138 is capable of detecting location data. The mobile processor 106 may receive the location data and compare it to map data, such as map data stored in the memory 108, in order to determine a current location of the modular smart necklace 100. In some embodiments, the mobile processor 106 may incorporate detected image data and/or other data (such as acceleration data from an accelerometer 146 of an accelerometer pod 144) into a determination of navigation instructions. In that regard, the navigation instructions may have a relatively high accuracy as compared with systems utilizing GPS units alone.

The accelerometer pod 144 may include the accelerometer 146. The accelerometer 146 may be a single-axis or a multiple-axis accelerometer, and may include more than one accelerometer. The accelerometer 146 can detect acceleration information along one, two, three, or more axes.

The modular smart necklace 100 may also include a network communication pod 140. The network communication pod 140 may include a network access device 142 and an antenna (not shown). The network access device 142 may include one or more of a Wi-Fi unit, a Bluetooth unit, a radio frequency identification (RFID) tag or reader, a physical Ethernet connector, a cellular network unit for accessing a cellular network (such as 3G or 4G), or the like. The network access device 142 may allow the modular smart necklace 100 to connect to another device or network for data downloads (such as updates to the main unit 102, updates to other pods, and/or image/audio downloads), and data uploads (such as status updates and/or image/audio uploads).

The modular smart necklace 100 may also include an alert pod 148. The alert pod 148 may include a pod processor 150 and a network access device 152 similar to the network access device 142 of the network communication pod 140. In some embodiments, the mobile processor 106 and/or the pod processor 150 may determine if a medical or safety alert should be generated based on data received from other pods, such as the camera pod 126 (i.e., image data corresponding to a fall or image data corresponding to a front view of a gun) or the accelerometer pod 144 (i.e., acceleration data corresponding to a fall). In some embodiments, the alert pod 148 may also include a button or other input that a user may depress or otherwise activate if an alert is desired.

If an alert is desired, the mobile processor 106 and/or the pod processor 150 may control the network access device 152 to transmit a medical alert. For example, the medical alert may include a recorded audio or text message, a beacon, or other signal to a predetermined medical or assistance team, such as a nearby hospital or a 911 call center. Thus, inclusion of the alert pod 148 provides a safety net for a user as the modular smart necklace 100 may detect an emergency and accordingly alert a responsible party.

In some embodiments, the alert pod 148 may not include the pod processor 150 such that the mobile processor 106 performs the logic functions, and in some embodiments, the alert pod 148 may not include the network access device 152 such that the signal is transmitted via the network access device 142 of the network communication pod 140.

The modular smart necklace 100 may also include a button pod 154. The button pod 154 may include one or more buttons 156 or other input devices for receiving user input. A user may control operation of the modular smart necklace 100 via the buttons 156. For example, the user may use the buttons 156 to switch between modes of the modular smart necklace 100, to start or stop an operation, or the like. In some embodiments, the buttons 156 may be positioned on one or more of a front, a side, a bottom, or a back of the button pod 154. In some embodiments, other types of inputs may be included such as a scroller, a touchpad, a switch, or the like.

The modular smart necklace 100 may also include a display pod 158 that includes a display 160. The display 160 may be an analog display, such as one or more light sources arranged in a predetermined format, or a digital display, such as an LCD or other digital display. In some embodiments, the display 160 may be a touchscreen capable of receiving input and displaying output. The display 160 may be electrically coupled to the mobile processor 106 and may output data as instructed by the mobile processor 106.

The modular smart necklace 100 may also include a biometric security pod 162 having a biometric sensor 164. The biometric sensor 164 may be capable of detecting one or more biometric measurements such as a fingerprint, a retina scan, a voice pattern, facial recognition, or the like. In some embodiments, the modular smart necklace 100 will not respond to user input until the biometric sensor 164 detects a biometric of an authorized user. For example, the memory 108 may store data corresponding to a biometric of one or more authorized users. The mobile processor 106 may receive the detected biometric from the biometric sensor 164 and compare it to the authorized biometric(s) stored in the memory 108. If a match is found, the mobile processor 106 may allow a user to interact with the modular smart necklace 100. However, if no match is found, the mobile processor 106 may prevent a user from interacting with the modular smart necklace 100.

In a similar aspect, each of the pods may include a memory capable of storing the authorized biometrics. In that regard, each of the pods may not respond to user input until an authorized biometric is detected by the biometric sensor 164. In other embodiments, the mobile processor 106 may control a logical switch on each of the pods which prevents the pods from responding to user input until the mobile processor 106 flips the switch to an "on" position in response to determining that a detected biometric is authorized. Accordingly, the modular smart necklace 100 and each of the pods thereof may be rendered useless if stolen.

The modular smart necklace 100 may also include a health pod 166. The health pod 166 may include a sensor 168 for detecting a heart rate, a number of steps and/or a respiration rate of the user. This information may be used when a user is working out to help the user ascertain whether he is meeting his exercise goals.

Each of the pods of the modular smart necklace 100 may have similar dimensions or different dimensions. For example, the outer casing 117 of the spacer pod 114 may have a length 174 that is greater than a length 170 of an outer casing 137 of the GPS pod 136 and a width 176 that is less than a width 172 of the outer casing 137 of the GPS pod 136. In some embodiments, spacer pods may be provided having various lengths and widths so that the modular smart necklace 100 can be better fitted to users of various sizes and shapes.

In addition to spacer pods, other pods may be provided having various dimensions and shapes. For example, an outer casing 157 of the button pod 154 may have both a length 180 and a width 182 that is greater than the length 170 and width 172 of the GPS pod 136. In a similar aspect, some pods may be provided having various shapes. For example, an outer casing 147 of the accelerometer pod 144 may have a curvature so that it better aligns with the GPS pod 136 and the button pod 154. The various sizes and shapes of the pods may be based on various factors such as a desirable shape of a modular smart necklace, an amount of real estate required to for all components to fit with an outer casing, or the like. Similarly, one type of pod may be provided having different sizes or shapes such that it can be coupled between any other two pods or a pod and the main unit 102. For example, another accelerometer pod may have similar dimensions as the GPS pod 136.

Figure 2:
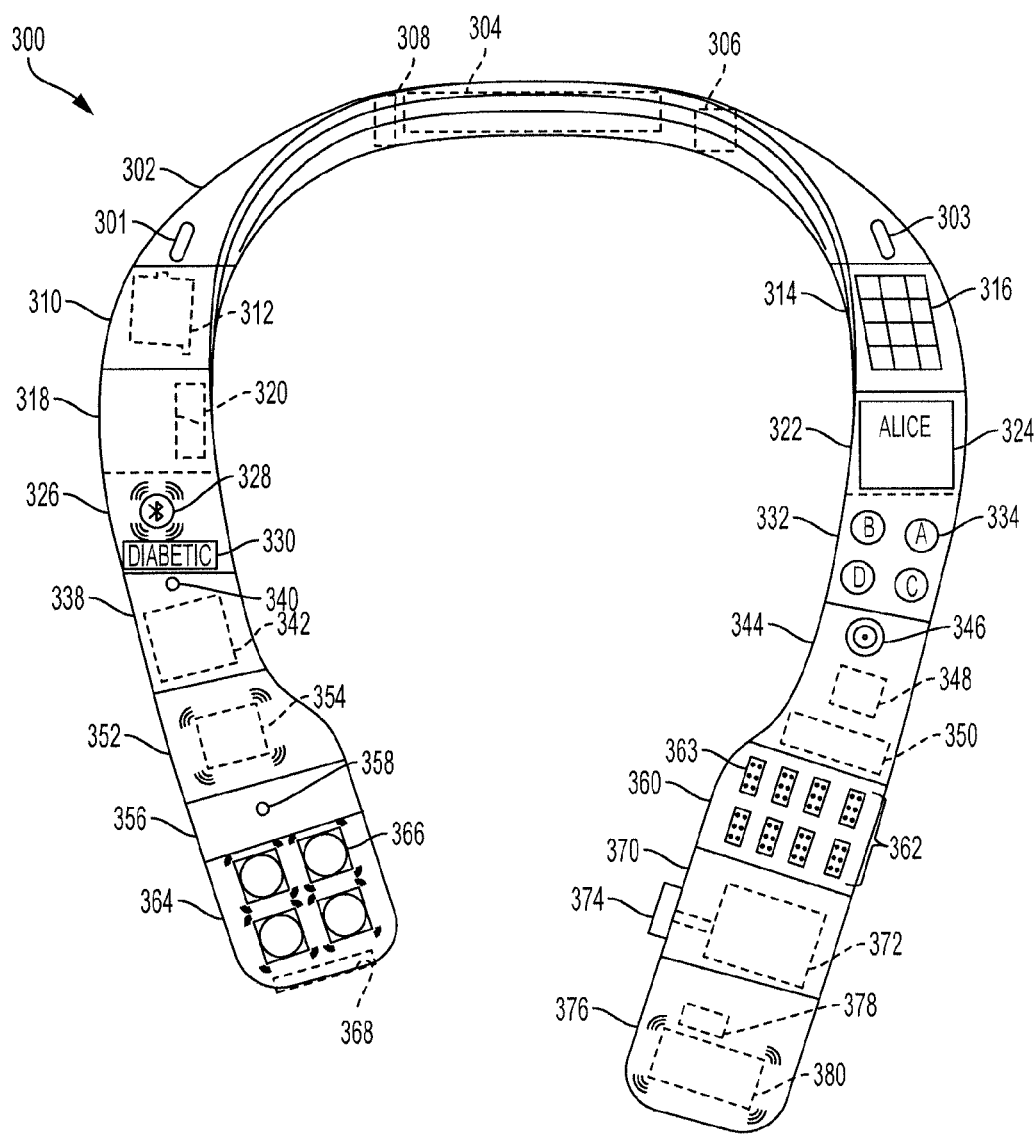
FIG. 2 illustrates another modular smart necklace having a main unit and a plurality of pods each having a component according to an embodiment of the present invention.

With reference now to FIGS. 1 and 2, a modular smart necklace 300 may include different pods than the modular smart necklace 100. The pods utilized in any modular smart necklace may be selected by a user. The modular smart necklace 300 includes a main unit 302 that includes different features than the main unit 102. The main unit 302 includes a battery 304, a processor 306, and a memory 308 that function similarly to the corresponding components of the modular smart necklace 100. The main unit 302, however, may also include a first speaker 301 and a second speaker 303 for providing audio output. Inclusion of the speakers 301, 303 in the main unit 302 allows the modular smart necklace 300 to provide audio without inclusion of audio pods.

With renewed reference to FIG. 2, the modular smart necklace 300 may also include a battery pod 310. The battery pod 310 may include a second battery 312 for providing power to the components of the main unit 302 and/or other pods. Inclusion of the battery pod 310 may extend an amount of time that the modular smart necklace 300 can be used without requiring external power.

The modular smart necklace 300 may also include a solar pod 314 including one or more solar cells 316. The solar cells 316 may receive sunlight and convert the sunlight into electrical power. The electrical power can be used to provide power to the components of the main unit 302 (for example by charging the battery 304) and/or the other pods.

The modular smart necklace 300 may also include a motion pod 318 including a motion-to-power converter 320. The motion-to-power converter 320 may be designed to convert kinetic energy into electrical power that can be used to provide power to the components of the main unit 302 and/or the other pods. For example, the motion-to-power converter 320 may use piezoelectricity technology or magnetic resonance technology to convert kinetic energy created by motion of a user to electrical power.

The modular smart necklace 300 may also include an information pod 322 that includes a display 324 and operates similarly to the display pod 158 and display 160 of FIG. 1. However, the information pod 322 may be programmed to constantly output predetermined information such as a user's name, a user's address, or the like.

The modular smart necklace 300 may also include an emergency display pod 326 having at least one of a display 330 or a machine readable output device 328, such as an RFID tag, a Bluetooth output device, or the like. The emergency display pod 326 may display or output emergency information such as current drugs prescribed to a user, medical conditions of the user, or the like. In that regard, in the case of an emergency, bystanders and/or medical personnel can receive helpful medical information.

The modular smart necklace 300 may also include a button pod 332 including buttons 334. With reference to FIGS. 1 and 3, the button pod 332 may include the same buttons as the button pod 154. However, the buttons 334 may be oriented in reverse order from the buttons 156. In that regard, button pods and/or any other pods may be designed for use by left handed or right handed individuals. For example, the orientation of the buttons 156 is such that they can be placed on a right side of the modular smart necklace 100 and used by a right-handed individual. The orientation of the buttons 334 is such that they can be placed on a left side of the modular smart necklace 300 and used by a left-handed individual in the same manner that the right-handed individual can use the buttons 156.

Returning to FIG. 2, the modular smart necklace 300 may also include a recorder pod 338 that includes an input device 340 and a memory 342. Input may be received by the input device 340 indicating that detected data should be stored. For example, when the input is received by the input device 340, any data collected by a microphone 358 of a microphone pod 356 may be stored in the memory 342 for later use. The recorder pod 338 may be used in conjunction with other pods, such as camera pods, GPS pods, or the like. This is advantageous if the user is at a concert or a presentation and wants to record audio or video for later use.

The modular smart necklace 300 may also include the microphone pod 356 that includes the microphone 358. The microphone 358 may detect audio data.

The modular smart necklace 300 may also include a significant other module 344 that includes an output device 346, a processor 348, and a memory 350. The memory 350 may include a pre-recorded text, audio, and/or video message. The pre-recorded message may be provided by a friend or relative of the user and may be specific to the particular user. The output device 346 may include a speaker, a display, and/or a vibration unit. The processor 348 may cause the output device 346 to output the pre-recorded message at a predetermined time, at predetermined time intervals, and/or in response to an input. In some embodiments, the pre-recorded message may be output using the main unit 302 and/or other pods.

The modular smart necklace 300 may also include a braille pod 360 including a refreshable braille display 362. The refreshable braille display 362 includes one or more braille cell 363 that includes 6 movable rods or pins that can each extend through an aperture defined within the braille cell 363. The 6 movable rods or pins of each braille cell 363 can be controlled to extend outward from the braille cell 363 or retract inward of the braille cell 363 such that each braille cell 363 can represent a braille character. Thus, the braille pod 360 can be used by a blind person to read text.

The modular smart necklace 300 may also include a tag module 364 including one or more removable tags 366 and a reader device 368. Each of the removable tags 366 may include a transmitter for transmitting a beacon, such as a Bluetooth signal or RFID signal. The reader device 368 may be capable of detecting the beacon of each of the removable tags 366 based on the received beacon. The reader device 368 and/or the processor 306 can use the beacon information to determine location information corresponding to each of the removable tags 366. The processor 306 may then output data using an output pod and/or other output device (such as the speakers 301, 303) to provide output data indicating the location of the removable tags 366. In one instance, a user may place one of the removable tags 366 in his wallet. If the wallet becomes misplaced, the user may provide an input to the modular smart necklace 300. The reader device 368 may then detect location data corresponding to the tag, such as a direction, a distance, a location on the map, or the like, and then the processor 306 may instruct an output device to output the location data.

The modular smart necklace 300 may also include a USB pod 370 that includes a memory 372 and a USB interface 374. The memory 372 may be a non-transitory memory capable of storing data received from the main unit 302 and/or another pod, and/or may store data received via the USB interface 374. In that regard, data from the modular smart necklace 300 can be transferred to a remote device by storing the data in the memory 372, connecting the USB interface 374 to the remote device, and transferring the data onto the remote device. Similarly, data from a remote device can be transferred to the modular smart necklace 300 by transferring the data onto the memory 372 via the USB interface 374, then transferring the data to the main unit 302 and/or a pod of the modular smart necklace 300. The USB interface can include a male or female USB interface, a traditional or mini USB interface, or another interface altogether.

The modular smart necklace 300 may also include a telepresence pod 376 including a pod processor 378 and a network access device 380. The pod processor 378 and the network access device 380 may be used to establish a communication with a remote device, such as a phone or computer of a friend or family member. The pod processor 378 may receive data from an input pod, such as the microphone pod 356, and transmit it to the remote device via the network access device 380. The network access device 380 may also receive data, such as image or audio data, and output it using an output pod and/or any other output device, such as the speakers 301, 303. In that regard, the telepresence pod 376 allows a user to communicate with other individuals.

Figure 3A:
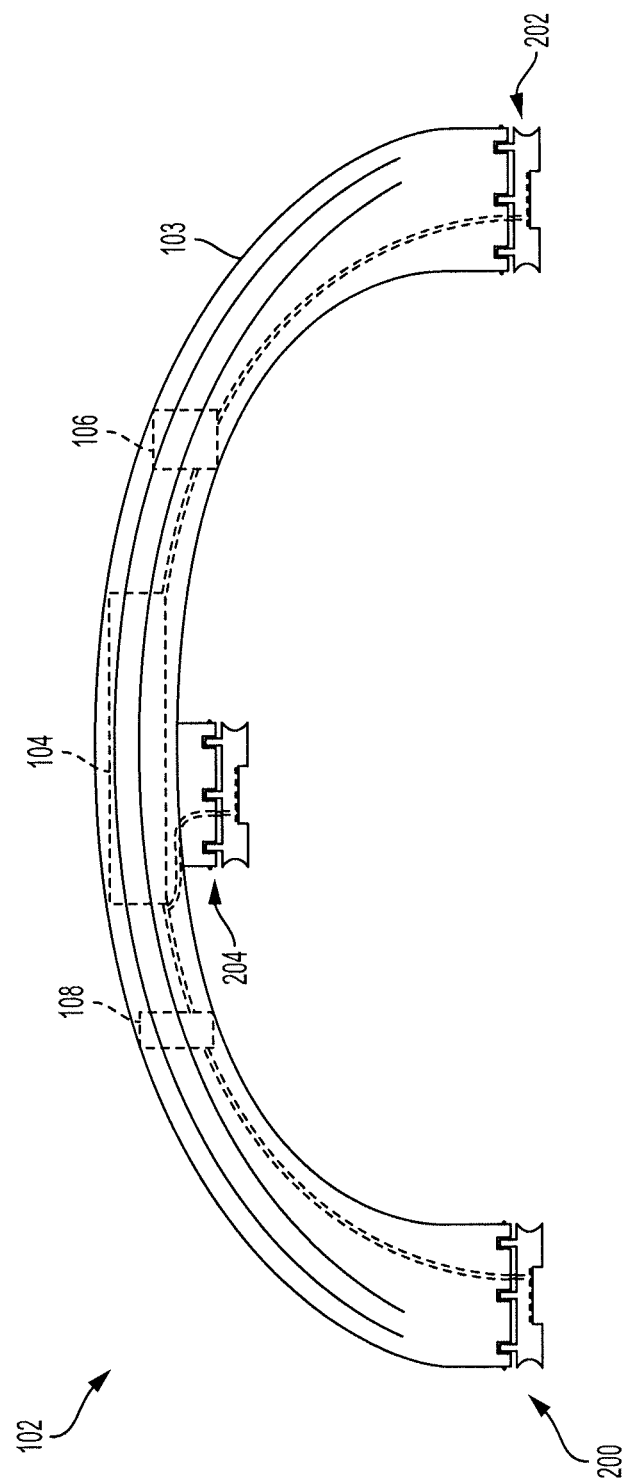
FIG. 3A the main unit of the modular smart necklace of FIG. 1 including three connectors according to an embodiment of the present invention.

With reference now to FIGS. 1 and 3A, the main unit 102 may include one or more connectors for connecting to various pods. The main unit 102 includes a first connector 200 on a first end of the main unit 102, a second connector 202 on a second end of the main unit 102, and a third connector 204 positioned between the first connector 200 and the second connector 202. The main unit 102 may include greater or fewer connectors than shown in FIG. 3A.

A user may connect one or more pods to each of the first connector 200 and the second connector 202 such that the pods may extend across a user's shoulders and potentially down a user's chest. Additionally, a user may connect one or more pods to the third connector 204 such that the pods may extend down a user's back from the main unit 102. The location of the third connector 204 may provide advantages in various situations. For example, when used by a police officer, a camera pod may be connected to the third connector 204 and the mobile processor 106 may be designed to generate an output to alert the police officer if something is approaching his back.

Figure 3B:
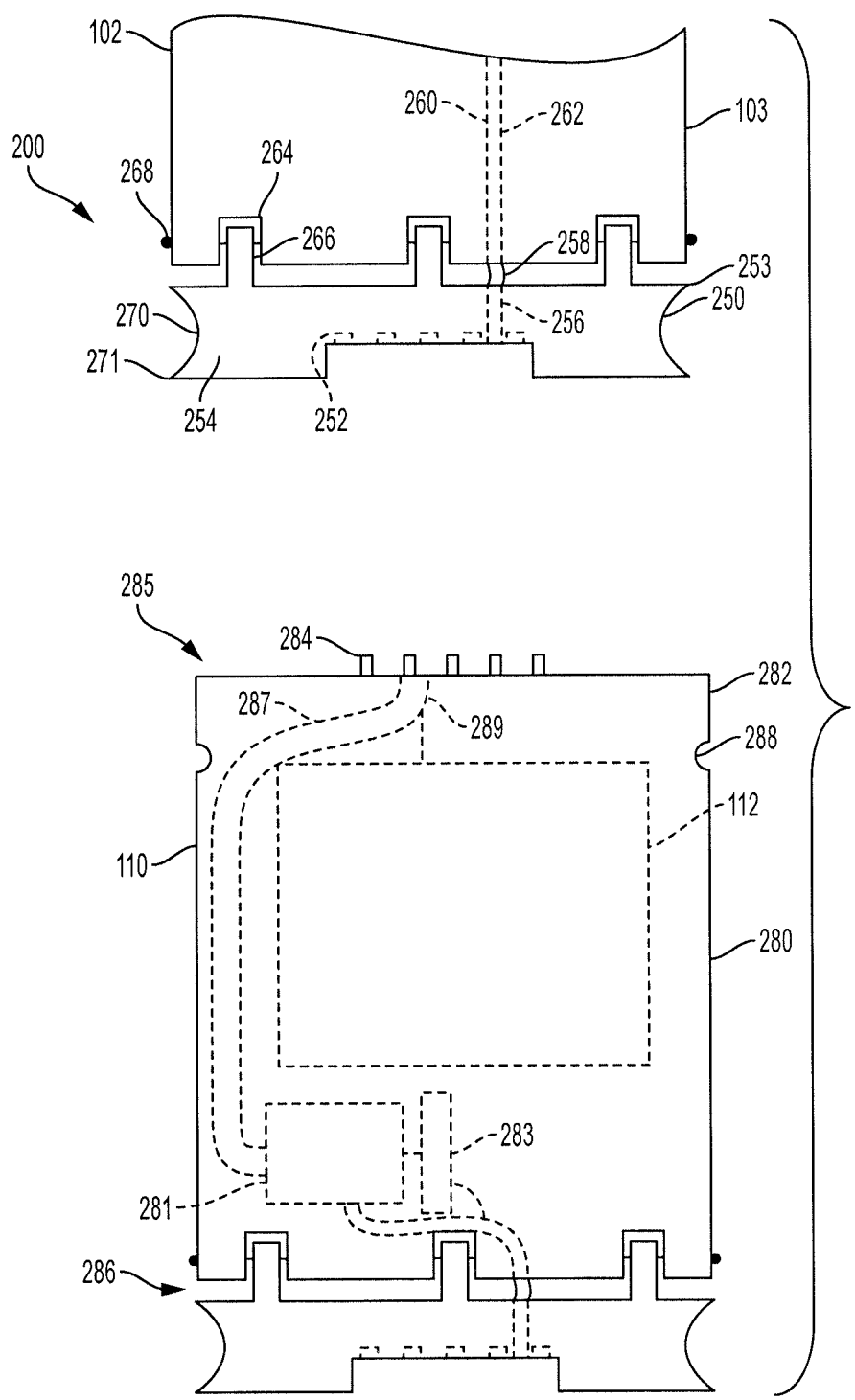
FIG. 3B illustrates one of the connectors of the main unit of FIG. 3A and a vibration pod having a connector for mating with the connector of the main unit according to an embodiment of the present invention.

With reference now to FIG. 3B, the first connector 200 of the main unit 102 may include a receptacle 250 pivotably coupled to the outer casing 103 of the main unit 102. The outer casing 103 of the main unit 102 may include one or more pivot cavities 264 extending towards a center of the outer casing 103. The receptacle 250 may include a receptacle casing 253 defining one or more fingers 266 extending into the pivot cavities 264. The area of the outer casing 103 on either side of each of the pivot cavities may define an opening (not shown) extending across the width of the outer casing 103. Each of the fingers 266 may also define an opening (not shown) extending across the width of each of the fingers 266. The openings of the outer casing 103 and the fingers 266 may be aligned and a pin 268 may be inserted therethrough. The pin 268 may be coupled in place using a locking mechanism such as a nut, a screw, a lock-pin, or other connector to reduce the likelihood of the pin 268 becoming removed. In that regard, the pin 268 may cause the receptacle casing 253 to be pivotably coupled to the outer casing 103 (i.e., the receptacle casing 253 and the outer casing 103 may pivot relative to each other about the pin 268).

The receptacle 250 may include one or more sockets 252 or other contacts for allowing propagation of data and/or power signals. The sockets 252 may be coupled to a flexible cable 258 via one or more wires 256 or other connections within the receptacle 250. The flexible cable 258 may be connected to the battery 104 via one or more power lines 260 and to the mobile processor 106 and/or the memory 108 via one or more data lines 262. The flexible cable 258 may be designed to bend as the receptacle 250 pivots relative to the main unit 102, extending the life of the flexible cable 258.

The receptacle casing 253 may define a snap-fit cavity 254 designed to receive a connector 285 of the vibration pod 110. The connector 285 may be considered a proximate connector as it is on an end of the vibration pod 110 that is proximate to the main unit 102. The connector 285 may include a plug 282 including one or more pins 284 or other contacts and one or more indentations 288. The plug or a component connected thereto may be partially compressible such that it can be compressed across its width (i.e., towards the pins 284).

In order to connect the vibration pod 110 to the main unit 102, the plug 282 may be compressed across its width and inserted into the receptacle 250. As the plug 282 is positioned within the snap-fit cavity, each of the sockets 252 may receive one of the pins 284, creating an electrical connection between the vibration pod 110 and the main unit 102. Additionally, the shape of the snap-fit cavity 254 may allow the plug 282 to decompress such that the indentations 288 may receive edges 271 of the receptacle casing 253. This reduces the likelihood of the plug 282 being inadvertently removed from the receptacle 250. In order to remove the plug 282 from the receptacle 250, the plug 282 may be compressed through openings 270 of the receptacle casing 253. As the plug 282 is compressed, the indentations 288 release the edges 271 such that the plug 282 may be removed from the receptacle casing 253.

The pins 284 may be electrically connected to one or more components of the vibration pod. For example, the vibration pod 110 can include a pod processor 281 and a memory 283 that are coupled to the pins 284 via one or more data lines 287 and one or more power lines 289. In addition to being coupled to the pod processor 281 and the memory 283, the data lines 287 and/or power lines 260 may also be electrically connected to a second, or distal, connector 286 of the vibration pod 110. This allows another pod to be connected to the connector 206 and receive power and data signals from the main unit 102 via the vibration pod 110. The connector 286 may be considered a distal connector as it is positioned on an end of the vibration pod 110 that is distal to the main unit 102. The second connector 286 may have similar features as the first connector 200. For example, the distal connector 286 may be designed to pivotably attach to another connector and may allow transmission of data and/or power signals.

Returning to discussion of the components of the vibration pod 110, the power lines 289 may supply power to the vibration unit 112, the pod processor 281, and/or the memory 283. Similarly, the data lines 287 may be connected to the pod processor 281. The pod processor may be electrically coupled to and designed to control the vibration unit 112 based on data received via the data lines 287 from the mobile processor 106 of FIG. 1. In some embodiments the pod processor 281 may regulate the transmission of the power signals through the vibration pod 110.

The pod processor 281 may be a mobile computing processor such as an ARM processor, DSP processor, distributed processor, or other form of central processing. The pod processor 281 may be designed to have a smaller footprint than the mobile processor 106 of FIG. 1 and may include different functionality.

The memory 283 may be one or any combination of the following: a RAM or other volatile or nonvolatile memory, a non-transitory memory or a data storage device, such as a hard disk drive, a solid state disk drive, a hybrid disk drive, or other appropriate data storage, and may further store machine-readable instructions, which may be loaded into the memory 283 and executed by the pod processor 281.

Together, the pod processor 281 and the memory 283 may convert data between the mobile processor 106 of FIG. 1 and the vibration unit 112 in order to control functionality of the vibration unit 112. For example, the pod processor 281 may receive a relatively high-level instruction from the mobile processor 106 of FIG. 1, such as an instruction to cause vibration for one second. The pod processor 281 may convert the high-level instruction to low-level code, such as machine code, that is usable to control the vibration unit 112. Continuing the example, the pod processor 281 may then use the low-level code to control the vibration unit 112 to cause the vibration unit 112 to vibrate for one second.

Figure 3C:
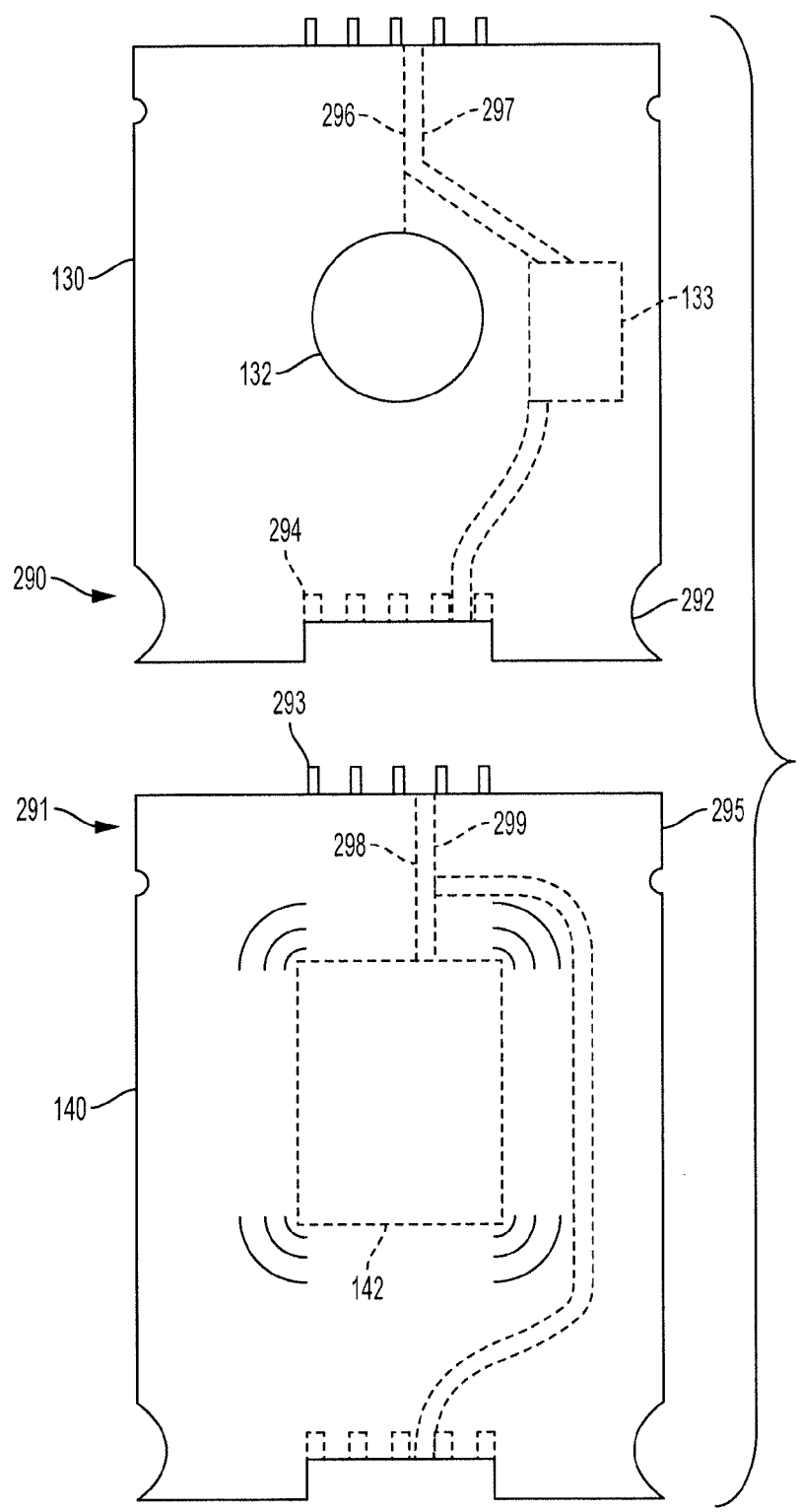
FIG. 3C illustrates a camera pod having a connector and a network communication pod having a connector for mating with the connector of the camera pod according to an embodiment of the present invention.

With reference now to FIGS. 3B and 3C, the camera pod 130 may have a distal connector 290 that is different from the distal connector 286 of the vibration pod. The distal connector 290 may include all of the features of the connector 286 with the exception of the features allowing relative pivoting of the pods. The network communication pod 140 may include a proximate connector 291 that includes all of the features of the proximate connector 285 of the vibration pod 110. In that regard, a receptacle 292 of the camera pod 130 may include sockets 294 that receive pins 293 of a plug 295 of the connector 291 of the network communication pod 140, allowing electrical communication between the camera pod 130 and the network communication pod 140.

In some embodiments all of the pods include pivotable connectors, in some embodiments some of the pods include pivotable connectors, and in some embodiments none of the pods include pivotable connectors. In some embodiments, each of the plugs can connect to any of the receptacles and vice versa. This allows the location of each of the pods to be determined by the user.

As with the vibration pod 110, the camera pod 130 includes the pod processor 133. Unlike the vibration pod 110, the camera pod 130 does not include a memory. In that regard, the pod processor 133 may have an internal memory, may have hardware designed to perform a specific task(s), or may access instructions from the memory 108 of FIG. 1.

The pod processor 133 may receive a power signal from power lines 296 and/or a data signal from data lines 297. The camera 132 may also receive the power signal from the power lines 296 but may not be coupled to the data lines 297. Instead, the pod processor 133 may control operation of the camera 132 and/or receive detected image data from the camera 132. As with the vibration pod 110, the pod processor 133 may or may not regulate the transmission of the power signals within the camera pod 130.

Power lines 298 and data lines 299 of the network communication pod 140 are connected to the power lines 296 and the data lines 297 of the camera pod 130 via the distal connector 290 and the connector 291. The data and power signals may pass through the network communication pod 140 in a similar manner as the power lines 296 and the data lines 297 of the camera pod 130. The network access device 142 may also be coupled to and receive power via the power lines 298 and be coupled to and transmit/receive data via the data lines 299.

One skilled in the art will realize that various connections between pods can be used without departing from the scope of the disclosure. In some embodiments, connections between pods include a mechanical and electrical connection and may or may not include a feature for allowing adjacent pods to pivot or rotate relative to each other.

Figure 4A:
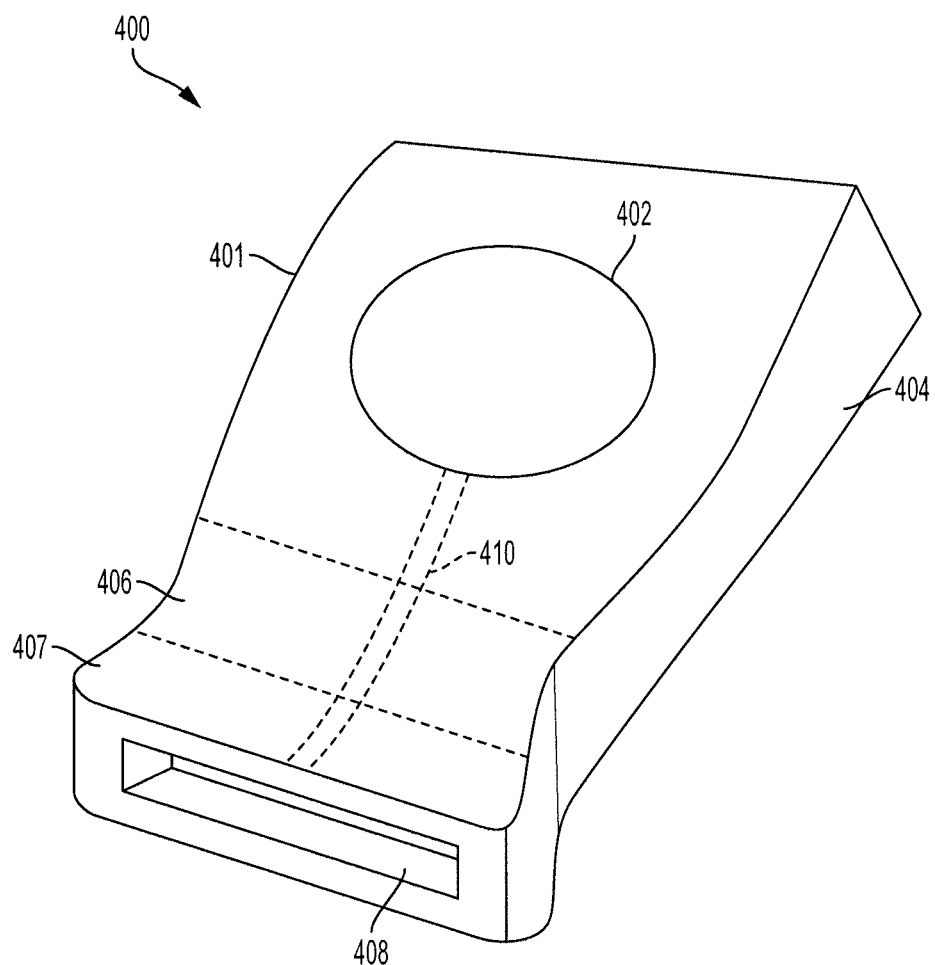
FIGS. 4A-4D illustrate various connectors that can be used between pods for electrical and/or mechanical connections according to embodiments of the present invention.

With reference now to FIGS. 4A-4D, alternative exemplary connectors between pods are shown. Turning now to FIG. 4A, a camera pod 400 may have an outer casing 401 and a camera 402 coupled to the outer casing 401. The outer casing 401 may include a first rigid portion 404, a second rigid portion 407 and a flexible portion 406 therebetween. The camera 402 may be coupled to the first rigid portion 404. The second rigid portion 407 may define a receptacle 408 of a connector, such as a snap connector. In that regard, the receptacle 408 may be used to physically and/or electrically couple the camera pod 400 to another pod.

The flexible portion 406 may include rubber or another flexible material that allows the second rigid portion 407 to move relative to the first rigid portion 404. In that regard, a pod coupled to the receptacle 408 may rotate and/or pivot relative to the first rigid portion 404. A wire or cable 410 may be coupled to the receptacle 408 and to the camera 402 and extend through the flexible portion 406. In that regard, another pod can communicate with the camera 402 via the receptacle 408 and the wire or cable 410.

Figure 4B:
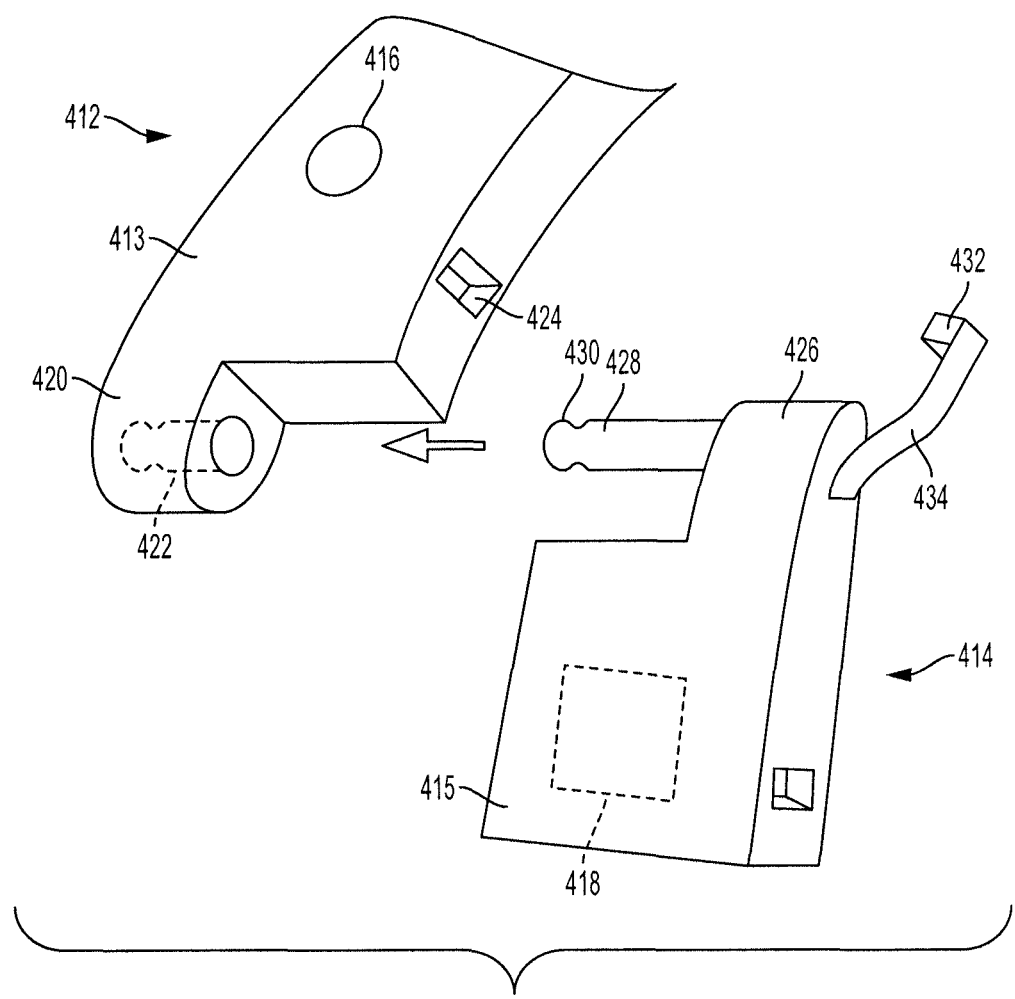

Turning to FIG. 4B, a camera pod 412 may be designed to connect to a processing pod 414. The camera pod 412 includes a camera 416 and the processing pod 414 includes a processor 418. The camera pod 412 includes an outer casing 313 defining an extension 420 extending downward and away from the camera 416. The extension 420 further defines, a mechanical socket 422. The camera pod 412 also includes an electrical receptacle 424 coupled to the outer casing 413.

The processing pod 414 also includes an extension 426 extending upward and away from the processor 418. A mechanical plug 428 extends perpendicular from the extension 426 and includes a nipple 430. The mechanical plug 428 is designed to mate with the mechanical socket 422. In that regard, the nipple 430 can be received by a feature within the mechanical socket 422, mechanically coupling the mechanical plug 428 and the mechanical socket 422. When coupled in this manner, the processing pod 414 can pivot relative to the camera pod 412.

The processing pod 414 also includes an electrical plug 432 connected to the outer casing 415 by a flexible strap 434. The flexible strap 434 may include a flexible material, such as rubber, and wires or cables extending therethrough and transferring electrical signals. The electrical plug 432 is designed to mate with the electrical receptacle 424. In that regard, the electrical connection allows data to transfer between the camera pod 412 and the processing pod 414. The flexible strap 434 allows the processing pod 414 to pivot with respect to the camera pod 412 without disturbing the electrical connection. Although the electrical plug 432 and the electrical receptacle 424 are positioned on the sides of the pods, electrical connectors can be placed on a front, a back, a top, a bottom, and/or the other sides of the pods.

Figure 4C:
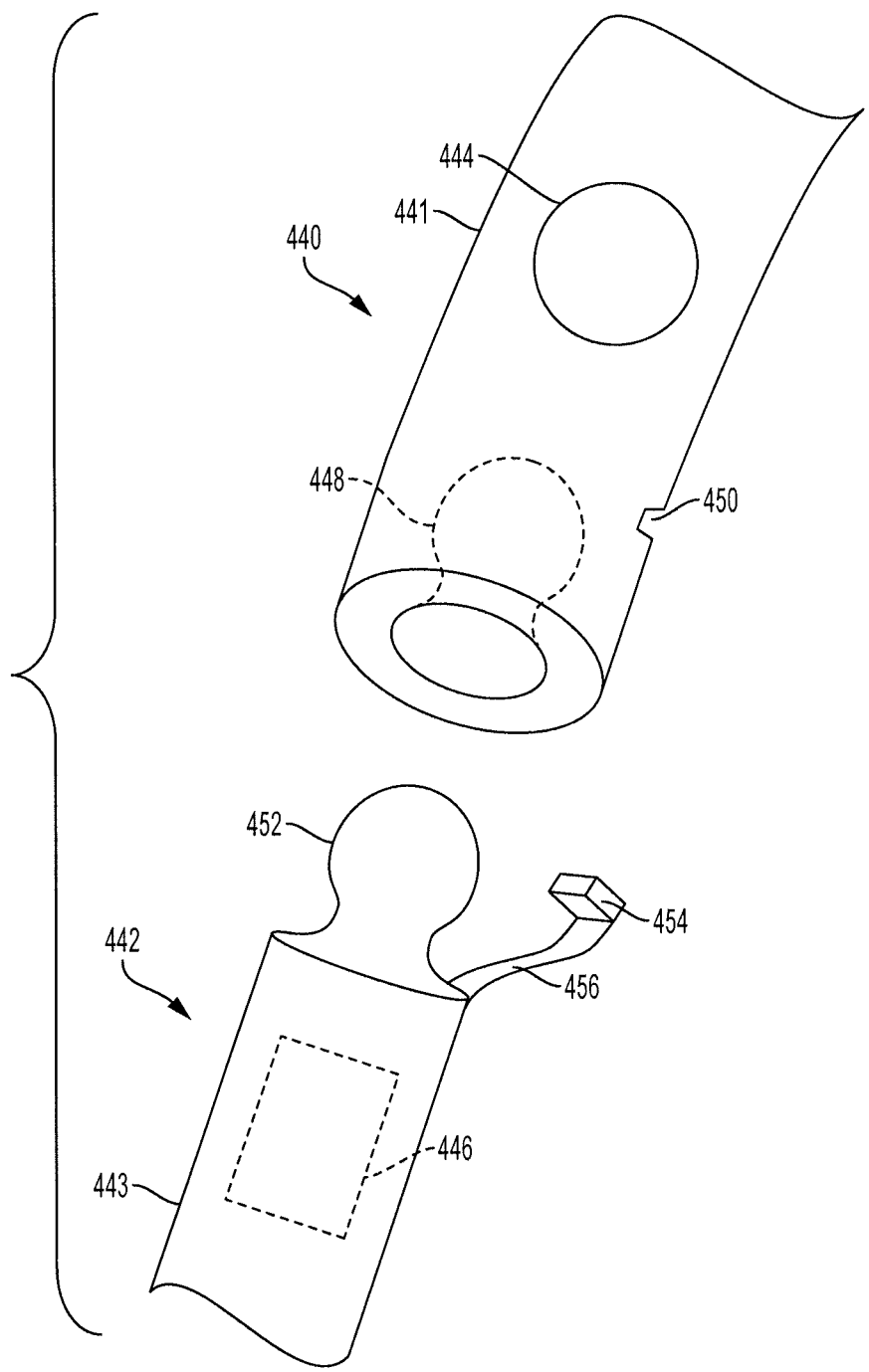

Turning now to FIG. 4C, a camera pod 440 and a processing pod 442 are designed to mate with one another. The camera pod 440 and the processing pod 442 have outer casings 441 and 443, respectively that have a cylindrical shape instead of a rectangular shape. The camera pod 440 includes a camera 444 and the processing pod 442 includes a processor 446.

The outer casing 441 of the camera pod 440 defines a ball socket 448 and includes an electrical socket 450. The outer casing of the processing pod 442 defines a ball 452 and is coupled to an electrical plug 454. The ball 452 is designed to be received by the ball socket 448, mechanically coupling the camera pod 440 and the processing pod 442. When coupled, the ball socket 448 and the ball 452 allows the processing pod 442 to pivot and/or rotate with respect to the camera pod 440.

The electrical plug 454 is configured to mate with the electrical socket 450, thus electrically coupling the camera pod 440 and the processing pod 442. The electrical plug 454 is coupled to the outer casing 443 of the processing pod 442 via a flexible strap 456 that allows the electrical connection to remain undisturbed when the processing pod 442 moves relative to the camera pod 440.

Figure 4D:
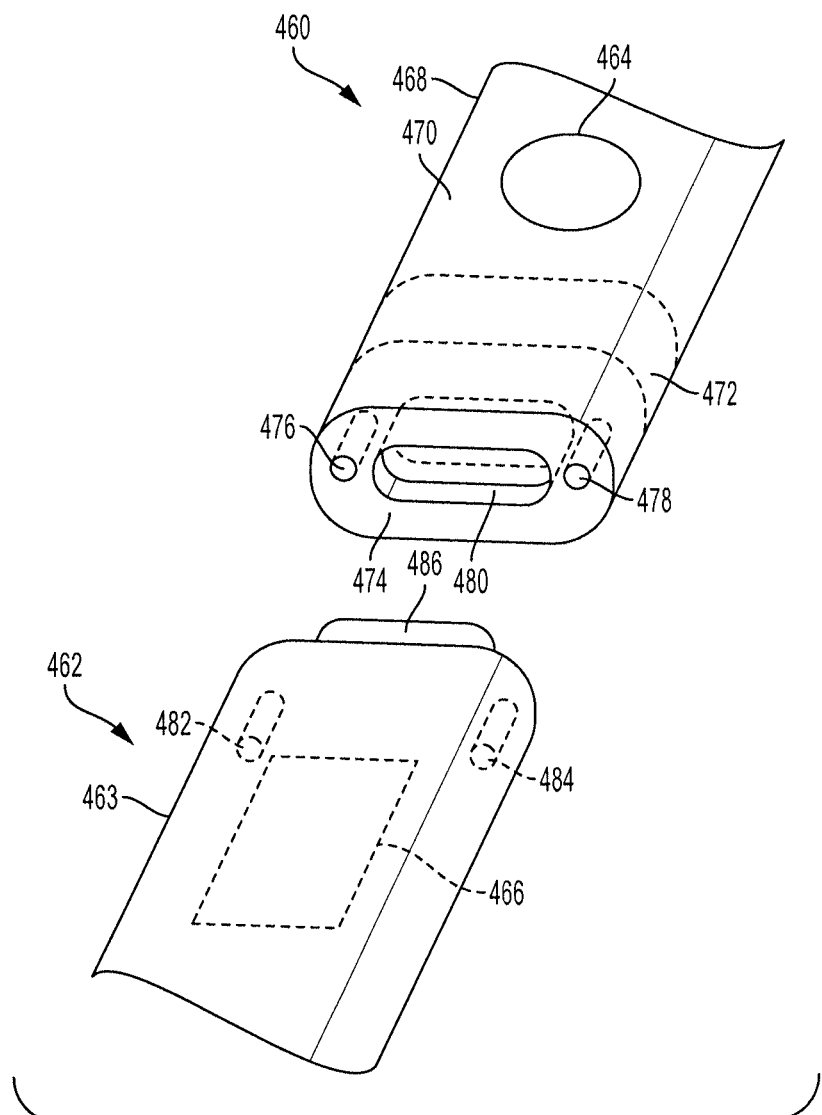

Turning now to FIG. 4D, a camera pod 460 is configured to mate with a processing pod 462. The camera pod 460 includes a camera 464, and the processing pod 462 includes a processor 466. The camera pod 460 includes an outer casing 468 having a first rigid portion 470, a second rigid portion 474, and a flexible portion 472 therebetween, allowing the first rigid portion 470 to rotate and/or pivot with respect to the second rigid portion 474. The second rigid portion includes a first magnet 476, a second magnet 478 and an electrical receptacle 480.

The processing pod 462 includes an outer casing 463 and a first magnet 482 and a second magnet 484 coupled thereto. The outer casing 463 also includes and/or defines an electrical plug 486. The processing pod 462 can be connected to the camera pod 460 by inserting the electrical plug 486 into the electrical receptacle 480 and aligning the first magnets 476, 482 with the second magnets 478, 484. When aligned and relatively near each other, the magnets of each pod attract, coupling the pods together. Electrical signals can transfer between the pods via the electrical plug 486 and the electrical receptacle 480 when connected and the flexibility of the flexible portion 472 allows the processing pod 462 to pivot and/or rotate with respect to the first rigid portion 470 of the outer casing 468 of the camera pod 460.

Figure 5:
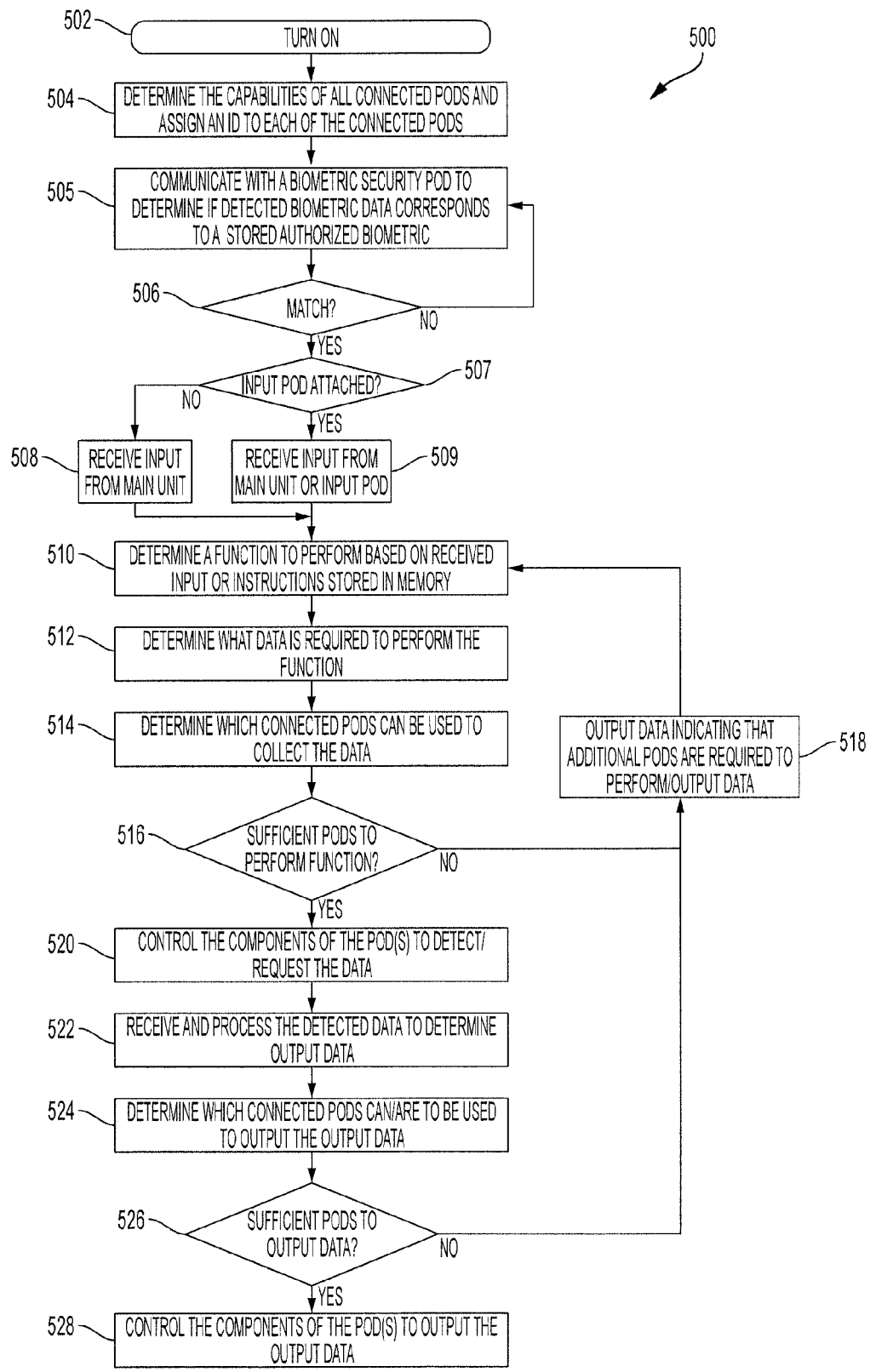
FIG. 5 is a flow chart illustrating a method to be performed by a processor of a modular smart necklace according to an embodiment of the present invention.

With reference now to FIG. 5, a method 500 for controlling a modular smart necklace by a processor of a main unit, such as the mobile processor 106 of the main unit 102 of FIG. 1 or the processor 306 of the main unit 302 of FIG. 2, begins in block 502 when the modular smart necklace is turned on. In block 504, the processor may determine the capabilities of all of the connected pods and assign an identifier to each of the connected pods. The identifier may be used by the processor to transmit instructions to the proper pod.

In block 505, the processor may communicate with a biometric security pod to determine if the biometric security pod received a biometric that corresponds to an authorized biometric. In block 506, the processor may determine whether the received biometric matches an authorized biometric in memory.

If a match is found, the processor may allow the modular smart necklace to be used. In block 507, the processor may determine whether an input pod is attached to the modular smart necklace. If an input pod is not attached, the processor may receive an input from the main unit at 508. If an input pod is attached, the processor may receive an input from the main unit and/or the input pod at 509. In some embodiments, the processor may perform functions without user input, such as based on instructions stored in a memory.

In block 510, the processor may receive an input from an input pod and/or may function based on instructions stored in the memory. Based on the input/instructions, the processor may determine a function to be performed such as providing navigation instructions, communicating with a remote device, or the like.

In block 512, the processor may determine what data is required and what data is desired for performing the function. For example, if the function is navigation, the processor may require location data and may desire image data and acceleration data. In block 514, the processor may determine which connected pods can be used to provide the data. For example, a GPS pod can provide the location data, a camera pod can be used to provide the image data, and an accelerometer pod can be used to provide the acceleration data. If the required pods are not available at block 516, the processor instructs an output pod to output data indicating that additional pods are required to perform the desired function at block 518.

At block 520, the processor may control the components of the pods to detect and/or request any required and desired data. At 522, the processor may receive the detected data and process the data in order to determine output data. For example, the output data may include navigation instructions.

At 524, the processor may determine which connected pods can be used to output the output data and which pods are preferred. At 526, if sufficient pods are not available to output the output data, the processor may attempt to output data indicating that additional pods are required to output the data in block 518. In block 528, the processor may control the components of the output pods to output the output data.

With reference now to FIG. 6, each of the main unit and the various pods of a modular smart necklace may be sold separately or may be sold in kits. Each of the kits may or may not include a main unit. For example, a kit may be sold having a main unit and a collection of pods and another kit may be sold having the collection of pods without a main unit. Each of the kits may include pods suited for a particular purpose. In some embodiments, each of the kits may include software to be loaded onto the mobile processor of the main unit for performing pod and/or kit-specific functions and data to be used in performing the pod/kit-specific functions. In some embodiments, each of the pods may include software loaded onto a pod processor or memory, and/or to be loaded onto the mobile processor for performing pod specific and/or kit specific functions.

A chart 600 illustrates various kits including the name and purpose of the kit, standard pods included in the kit, and optional pods that may or may not be included with the kit. Each of the kits may include all of the included pods. Some kits may include none of the optional pods, some kits may include some of the optional pods, and some kits may include all of the optional pods. The kits are not limited to the included and optional pods illustrated by the chart 600.

An exercise kit may include an accelerometer pod, a health pod, and a motion pod. The accelerometer pod may detect an acceleration of the modular smart necklace. This information can be used in conjunction with a processor to determine a distance traveled, an estimation of energy burned, a speed, or other information that may be used to provide quantitative statistics regarding a user's workout. The health pod may include a heart rate sensor and/or a respiration rate sensor. The heart/respiration rate sensors may be used to detect health metrics of the user while he is exercising. This may be useful to the user as it can help the user achieve a desired heart and/or respiration rate, inform the user of his current heart and/or respiration rate, and/or may be used by the processor to determine whether the user is approaching a hazardous respiration/heart rate. The motion pod may include a motion-to-power converter which may collect the kinetic energy generated by the user's exercise.

The exercise kit may optionally include an emergency display pod. This may be desirable if the user is in poor health. For example, an elderly person having a history of heart problems may the emergency display pod so that his health information is available should become unconscious.

A navigation kit may include a camera pod, an accelerometer pod, a GPS pod, and an output pod. The camera pod can be used to detect image data corresponding to a surrounding environment of the modular smart necklace, the accelerometer pod can be used to detect acceleration data corresponding to an acceleration of the modular smart necklace, and the GPS pod can be used to detect location information corresponding to a location of the modular smart necklace. The output pod may include one or more speakers, vibration units, and/or displays and may be optional if the main unit includes output components such as vibration units or speakers.

The processor of the main unit may receive the image data, the acceleration data, and the location data and use this data to provide navigation instructions. Use of the image data and acceleration data allow for more precise navigation instructions that use of a GPS unit alone, especially for indoor environments and walking directions.

The navigation kit may optionally include a battery pod for storing extra power to ensure that the modular smart necklace has sufficient power to complete the navigation. The navigation kit may also optionally include an emergency display pod for displaying emergency information in the case that the user has health concerns or is traveling in a dangerous or unhealthy area. The navigation kit may also optionally include a telepresence pod so that the user can contact a resource for help if the user gets lost and cannot find a route.

A blind kit for use by vision-disabled individuals can include a camera pod, an accelerometer pod, an output pod, a telepresence pod, and optionally an input pod and a braille pod. The camera pod allows image data regarding the user's environment to be detected and the accelerometer pod can detect accelerations of the user. Used in conjunction, the image data and the acceleration data can be used to detect an environment of a user and the user's location relative to the environment. The image data can also be used to identify objects in the user's environment. The mobile processor can then provide information regarding the environment to the user using the output pod. The telepresence pod allows the user to communicate with a resource if the user becomes disoriented or requires assistance. The input pod may provide a specialized form of input that may be relatively easy to use without sight. For example, the input pod may include a plurality of buttons, each having a different shape such that the user can determine which button he is selecting based on feel alone. The braille pod allows the user to read text. For example, image data of text can be received by the processor of the main unit and converted to braille data to be output using the braille pod.

A sporting event kit can include a camera pod, a recorder pod, a network communication pod, an output pod, and optionally a USB pod. The camera pod can be used in conjunction with the recorder pod to record particular segments or "plays" of a sporting event. The user can then immediately re-watch the recorded image data using a display output pod and/or can watch the recorded image data from another device by transferring the recorded data via the optional USB pod. The network communication pod can allow the user to receive broadcasts or webcasts of any concurrent sporting events that the user is not attending.

A police use kit may include a main unit having a third connector, two camera pods, a recorder pod, and an output pod. One of the camera pods can be connected to the third connector of the main unit to detect image data corresponding to an area behind the police officer. Accordingly, the output pod can alert the officer if an unknown object or person is approaching the officer from the back. The other camera pod can be facing forward from the officer and used in conjunction with the recorder pod to detect and record image data corresponding to interactions between the officer and civilians.

The police use kit may optionally include a network communication pod to allow the officer to report an incident, call for backup, receive dispatch messages, or the like. The kit may also include a battery pod to ensure that the modular smart necklace has sufficient power to be operable throughout the officer's shift. The kit can also include a GPS pod to be used in conjunction with a mobile processor to navigate the officer to a desired location, such as a location provided in a dispatch instruction.

Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A modular computing necklace comprising:
    a first pod having an outer casing, a proximate connector mechanically coupled to the outer casing, and a first component electrically coupled to the proximate connector and configured to at least one of receive input data or output data;
    a second pod having an outer casing, a proximate connector mechanically coupled to the outer casing, and a second component electrically coupled to the proximate connector and configured to at least one of receive input data or output data;
    a biometric security pod having an outer casing, a proximate connector mechanically coupled to the outer casing, and a biometric sensor configured to detect biometric information; and
    a main unit having:
        an outer casing having a curvature,
        a first connector coupled to the outer casing and configured to be removably, pivotably and electrically coupled to the proximate connector of at least one of the first pod, the second pod, or the biometric security pod,
        a second connector coupled to the outer casing and configured to be removably, pivotably and electrically coupled to the proximate connector of at least one of the first pod, the second pod, or the biometric security pod such that the outer casing of the main unit can rest on a back of a neck and the outer casing of at least one of the first pod, the second pod, or the biometric security pod can each rotate about a shoulder,
        a battery for providing power to the first component and the second component,
        a memory configured to store an authorized biometric, and
        a mobile processor electrically coupled to the first connector and the second connector and configured to:
            determine a desired function to be performed,
            determine that insufficient components exist when the mobile processor cannot perform the desired function using any components that are electrically connected to the mobile processor,
            output a notification via at least one of the first pod or the second pod indicating that additional components are required for the mobile processor to perform the desired function when the insufficient components exist,
            receive the input data from at least one of the first pod or the second pod,
            determine output data based on the received input data and the desired function to be performed when sufficient components exist,
            output the output data via at least one of the first pod or the second pod when the sufficient components exist, and
            prevent the output data from being output when the detected biometric information fails to match the stored authorized biometric.

2. The modular computing necklace of claim 1, further comprising a third pod having an outer casing and a proximate connector mechanically coupled to the outer casing and a fourth pod having an outer casing and a proximate connector coupled to the outer casing, and wherein the first pod further includes a distal connector configured to be removably and electrically coupled to the proximate connector of the third pod and the second pod further includes a distal connector configured to be removably and electrically coupled to the proximate connector of the fourth pod.

3. The modular computing necklace of claim 2, wherein the outer casing of the third pod and the outer casing of the fourth pod are each configured to extend downward across the shoulder or a chest.

4. The modular computing necklace of claim 2, wherein the third pod further includes a third component electrically coupled to the proximate connector and the fourth pod further includes a fourth component electrically coupled to the proximate connector and wherein the mobile processor of the main unit is configured to communicate with each of the first component, the second component, the third component, the fourth component, and the biometric sensor via a pass through communication protocol.

5. The modular computing necklace of claim 1, further comprising a spacer pod having an outer casing, a proximate connector configured to be removably and electrically coupled to the first connector of the main unit, and a distal connector electrically connected to the proximate connector and configured to be removably and electrically coupled to the proximate connector of the first pod.

6. The modular computing necklace of claim 5, wherein the outer casing of the spacer pod is flexible such that it can bend to fit a contour of a body.

7. The modular computing necklace of claim 1, further comprising a third pod having an outer casing and a proximate connector mechanically coupled to the outer casing and wherein the main unit further includes a third connector coupled to the outer casing, positioned between the first connector and the second connector of the main unit, and configured to be removably and electrically coupled to the proximate connector of the third pod such that the third pod can extend down a back when coupled to the third connector of the main unit.

8. The modular computing necklace of claim 1, wherein the first pod or the second pod is a camera pod including a camera configured to detect image data, an output pod including at least one of a vibration unit, a speaker, or a display configured to output data, a microphone pod including a microphone configured to detect audio data, a network communication pod including a network access device configured to communicate with a second device via a network, a GPS pod including a GPS unit configured to detect location data, an accelerometer pod including an accelerometer configured to detect an acceleration, a solar pod including at least one solar cell configured to convert sunlight to electrical power, a motion pod including a motion-to-power converter configured to convert kinetic energy to electrical power, a health pod including at least one of heart rate sensor configured to detect a heart rate or a respiration sensor configured to detect a respiration rate, an emergency display pod including at least one of a display or a machine readable output device configured to display or output emergency information, an alert pod including at least one of a network access device or a pod processor configured to transmit an alert to an emergency contact, a name pod including a display configured to display a name, a telepresence pod including at least one of a network access device or a pod processor configured to allow communication with a third party via the camera pod and the output pod, a USB pod including a USB connector configured to connect to a remote device and a memory electrically coupled to the USB connector and configured to store data, a recorder pod including an input device configured to receive an input and a memory configured to store data in response to receiving the input, a significant other pod including a memory configured to store a message and at least one of including a second output device configured to output the message or a pod processor configured to transmit the message to another pod for outputting, a smart key pod including a smart key device configured to remotely control a remote device, a tag pod including a removable tag configured to transmit a beacon and a reader device configured to detect the beacon, a braille pod including a refreshable braille display configured to output data in braille format, or a button pod including at least one button configured to receive input data.

9. The modular computing necklace of claim 1, wherein the first pod further includes a pod processor electrically coupled to the first component and the mobile processor of the main unit and configured to convert data that is transmitted between the first component and the mobile processor of the main unit.

10. The modular computing necklace of claim 1, further comprising at least two camera pods each including a camera configured to detect image data and including a proximate connector configured to be electrically coupled to the main unit, wherein the mobile processor of the main unit is configured to determine stereo image data including distance information based on the detected image data from the at least two camera pods.

11. The modular computing necklace of claim 1, wherein:
one of the proximate connector of the first pod or the first connector of the main unit includes a receptacle that is pivotably connected to the outer casing and electrically connected to the outer casing via a flexible cable, and that includes:
  at least one socket electrically connected to the flexible cable, and
  a first physical connection feature; and
the other of the proximate connector of the first pod or the first connector of the main unit includes a plug that includes:
  a second physical connection feature configured to be removably connected to the first physical connection feature, and
  at least one pin configured to be received by and electrically connected to the at least one socket when the second physical connection feature is connected to the first physical connection feature.

12. A modular computing necklace comprising:
a camera pod having an outer casing, a distal connector mechanically coupled to the outer casing, a proximate connector mechanically coupled to the outer casing, and a camera electrically coupled to the proximate connector and configured to detect image data;
an accelerometer pod having an outer casing, a distal connector mechanically coupled to the outer casing, a proximate connector mechanically coupled to the outer casing, and an accelerometer configured to detect an acceleration;
an output pod having an outer casing, a distal connector mechanically coupled to the outer casing, a proximate connector mechanically coupled to the outer casing, and at least one of a speaker or a vibration unit configured to output data;
a biometric security pod having an outer casing, a distal connector mechanically coupled to the outer casing, a proximate connector mechanically coupled to the outer casing, and a biometric sensor configured to detect biometric information; and
a main unit having:
  an outer casing having a curvature,
  a first connector coupled to the outer casing and configured to be removably, pivotably and electrically coupled to the proximate connector of one of the camera pod, the accelerometer pod, the output pod, or the biometric security pod;
  a second connector coupled to the outer casing and configured to be removably, pivotably and electrically coupled to the proximate connector of one of the camera pod, the accelerometer pod, the output pod, or the biometric security pod, such that the outer casing of the main unit can rest on a back of a neck and the outer casing of each of the pods coupled to the first connector and the second connector can each rotate with a curve of a shoulder and the outer casing of one of the pods that is not directly coupled to the main unit can extend farther downwards across a chest or the shoulder than the pods that are directly coupled to the main unit,
  a battery for providing power to the camera and the at least one of the speaker or the vibration unit,
  a non-transitory memory configured to store at least one of map data or object data and to store an authorized biometric, and
  a processor electrically coupled to the first connector and the second connector and configured to:
    determine a desired function to be performed,
    determine that insufficient components exist when the processor cannot perform the desired function using any components that are electrically connected to the processor,
    instruct the at least one of the vibration unit or the speaker to output insufficient component information indicating that additional components are required for the processor to perform the desired function when the insufficient components exist,
    receive the detected image data and the detected acceleration,
    determine output data based on the image data and data, the acceleration, and the desired function to be performed when sufficient components exist,
    instruct the at least one of the vibration unit or the speaker to output the output data when the sufficient components exist, and
    prevent the output data from being output when the detected biometric information fails to match the stored authorized biometric.

13. The modular computing necklace of claim 12, wherein the output data includes at least one of object identification data based on the detected image data or navigation data based on the detected image data and the detected acceleration.

14. The modular computing necklace of claim 12, further comprising at least one of a microphone pod including a microphone configured to detect audio data, a network communication pod including a network access device configured to communicate with a second device via a network, a GPS pod including a GPS unit configured to detect location data, a solar pod including at least one solar cell configured to convert solar power to electrical power, a motion pod including a motion-to-power converter configured to convert kinetic energy to electrical power, a health pod including at least one of heart rate sensor configured to detect a heart rate or a respiration sensor configured to detect a respiration rate, an emergency display pod including at least one of a display or a machine readable output device configured to display or output emergency information, an alert pod including at least one of a network access device or a pod processor configured to transmit an alert to an emergency contact, a name pod including a display configured to display a name, a telepresence pod including at least one of a network access device or a pod processor configured to allow communication with a third party via the camera pod and the output pod, a USB pod including a USB connector configured to connect to a remote device and a memory electrically coupled to the USB connector and configured to store data, a recorder pod including an input device configured to receive an input and a memory configured to store data in response to receiving the input, a significant other pod including a memory configured to store a message and at least one of including a second output device configured to output the message or a pod processor configured to transmit the message to another pod for outputting, a smart key pod including a smart key device configured to remotely control a remote device, a tag pod including a removable tag configured to transmit a beacon and a reader device configured to detect the beacon, a braille pod including a refreshable braille display configured to output data in braille format, or a button pod including at least one button configured to receive input data.

15. The modular computing necklace of claim 12, further comprising a second camera pod including a second camera configured to detect additional image data and a proximate connector electrically coupled to the main unit, wherein the processor of the main unit is configured to determine stereo image data including distance information based on the detected image data from the camera pod and the second camera pod.

16. The modular computing necklace of claim 12, wherein:
one of the proximate connector of the camera pod or the first connector of the main unit includes a receptacle that is pivotably connected to the outer casing and electrically connected to the outer casing via a flexible cable, and that includes at least one socket electrically connected to the flexible cable and a first physical connection feature, and
wherein the other of the proximate connector of the camera pod or the first connector of the main unit includes a plug that includes a second physical connection feature configured to be removably connected to the first physical connection feature and at least one pin configured to be received by and electrically connected to the at least one socket when the second physical connection feature is connected to the first physical connection feature.

17. A kit for use with a modular computing necklace comprising:
a biometric security pod having a distal connector, a proximate connector, and a biometric sensor configured to detect biometric information;
a main unit having a first connector, a second connector, and a processor configured to:
determine a desired function to be performed,
determine that insufficient components exist when the processor cannot perform the desired function using any components that are electrically connected to the processor,
determine insufficient component information including a notification that additional components are required for the processor to perform the desired function when the insufficient components exist, and
prevent interaction with the modular computing necklace when the biometric security pod is disconnected from the main unit; and
a plurality of pods each having an outer casing, a distal connector, and proximate connector configured to be mechanically and electrically coupled to at least one of the first connector of the main unit or a distal connector of another pod, wherein the kit is at least one of:
a blind kit including:
a camera pod having a camera electrically coupled to the proximate connector and configured to detect image data,
an accelerometer pod having an accelerometer electrically coupled to the proximate connector and configured to detect an acceleration,
an output pod having at least one of a speaker or a vibration unit electrically coupled to the proximate connector and configured to output data received from the processor of the main unit when sufficient components exist and to output the insufficient component information when the insufficient components exist, and
a telepresence pod including at least one of a network access device or a pod processor electrically coupled to the proximate connector and configured to allow communication with a third party via the camera pod and the output pod;
a navigation kit including:
the camera pod,
the accelerometer pod,
the output pod, and
a GPS pod including a GPS unit electrically coupled to the proximate connector and configured to detect location data;
an exercise kit including:
the accelerometer pod,
a health pod having at least one of a heart rate sensor or a respiration sensor configured to detect a heart rate or a respiration rate, and
a motion pod including a motion-to-power converter electrically coupled to the proximate connector and configured to convert motion power to electrical power; or
a sporting event kit including:
the output pod,
the camera pod,
a network communication pod including a network access device electrically coupled to the proximate connector and configured to communicate with a second device via a network, and a recorder pod including an input device configured to receive an input and a memory configured to store the image data in response to receiving the input.

* * * * *